United States Patent
Payne et al.

(10) Patent No.: US 11,091,535 B2
(45) Date of Patent: Aug. 17, 2021

(54) THROMBIN INHIBITORS FOR TREATMENT OF STROKE AND RELATED COAGULATIVE DISORDERS

(71) Applicant: THE UNIVERSITY OF SYDNEY, Sydney (AU)

(72) Inventors: Richard J. Payne, Sydney (AU); Shaun Phillip Jackson, Sydney (AU); Pedro Jose Barbosa Pereira, Sydney (AU)

(73) Assignee: THE UNIVERSITY OF SYDNEY, Sydney (AU)

( * ) Notice: Subject to any disclaimer, the term of this patent is extended or adjusted under 35 U.S.C. 154(b) by 0 days.

(21) Appl. No.: 16/469,804

(22) PCT Filed: Dec. 15, 2017

(86) PCT No.: PCT/AU2017/051405
§ 371 (c)(1),
(2) Date: Jun. 14, 2019

(87) PCT Pub. No.: WO2018/107247
PCT Pub. Date: Jun. 21, 2018

(65) Prior Publication Data
US 2019/0367583 A1 Dec. 5, 2019

(30) Foreign Application Priority Data
Dec. 16, 2016 (AU) .................. 2016905231

(51) Int. Cl.
| A61K 38/08 | (2019.01) |
| A61K 38/10 | (2006.01) |
| A61K 38/00 | (2006.01) |
| C07K 7/06 | (2006.01) |
| C07K 7/08 | (2006.01) |
| A61P 7/02 | (2006.01) |
| C07K 14/81 | (2006.01) |

(52) U.S. Cl.
CPC ............ C07K 14/811 (2013.01); *A61K 38/00* (2013.01)

(58) Field of Classification Search
CPC ........ A61K 38/00; A61K 38/08; A61K 38/10; C07K 14/811; C07K 7/06; C07K 7/08; A61P 7/02
USPC ................ 530/300, 327; 514/1.1, 21.5, 21.6
See application file for complete search history.

(56) References Cited

U.S. PATENT DOCUMENTS

| 5,681,721 A | 10/1997 | Steffens et al. |
| 6,759,384 B1 | 7/2004 | Al-Obeidi et al. |
| 7,081,447 B2 | 7/2006 | Thurk |
| 7,423,021 B2 | 9/2008 | Thurk et al. |
| 2007/0298034 A9* | 12/2007 | Widom ............... C07K 16/2896 424/133.1 |
| 2009/0136444 A1 | 5/2009 | Priest et al. |
| 2012/0135931 A1* | 5/2012 | Kini ..................... C07K 14/811 514/13.7 |

FOREIGN PATENT DOCUMENTS

| DE | 4323754 | 12/1994 |
| JP | 2003116573 | 4/2003 |
| JP | 2008-532490 | 8/2008 |
| WO | WO 2001/000667 | 1/2001 |
| WO | WO 2001/038503 | 5/2001 |
| WO | WO 2003/022873 | 3/2003 |
| WO | WO 2004/063212 | 7/2004 |
| WO | WO 2007/067983 | 6/2007 |
| WO | WO 2010/128285 | 11/2010 |
| WO | WO 2012/024543 | 2/2012 |
| WO | WO 2014/194015 | 12/2014 |
| WO | WO 2014/194361 | 12/2014 |
| WO | WO 2016/042093 | 3/2016 |

OTHER PUBLICATIONS

Q86FP9 from UniProt, pp. 1-5. Integrated into UniProtKB/TrEMBL on Jun. 1, 2003. (Year: 2003).*
Esipov et al., "Comparative analysis of the effectiveness of C-terminal cleavage intein-based constructs in producing a recombinant analog of anophelin, an anticoagulant from Anopheles albimanus," *Appl. Biochem. Biotechnol.*, 175(5):2468-2488, 2015.
Li et al., "Platelet glycoprotein Ib alpha binds to thrombin anion-binding exosite II inducing allosteric changes in the activity of thrombin," *The Journal of Biological Chemistry*, 276(9):6161-6168, 2001.
Li et al., "Thrombin inhibition by serpins disrupts exosite II," *The Journal of Biological Chemistry*, 285(49):38621-38629, 2010.
PCT International Search Report and Written Opinioni issued in International Application No. PCT/AU2017/051405, dated Mar. 5, 2018.
Richardson et al., "Crystal structure of the human alpha-thrombin-haemadin complex: an exosite II-binding inhibitor," *The EMBO Journal*, 19(21):5650-5660, 2000.
Valenzuela et al., "Purification, cloning, and synthesis of a novel salivary anti-thrombin from the mosquito *Anopheles albimanus*," *Biochemistry*, 38(34):11209-11215, 1999.
Extended European Search Report issued in European Patent Application No. 17881550.2, dated Jun. 19, 2020.
Thompson et al., "Trifluoroethanethiol: An Additive for Efficient One-Pot Peptide Ligation-Desulfurization Chemistry," *Journal of the American Chemical Society*, 136(23):8161-8164, 2014.

(Continued)

*Primary Examiner* — Julie Ha
(74) *Attorney, Agent, or Firm* — Parker Highlander PLLC

(57) ABSTRACT

The treatment of stroke related diseases are described herein. In addition, fibrin clot formation and related activity is proposed for the disclosed compounds, in particular, peptides for inhibiting or modifying the cleavages of fibrinogen by thrombin. Methods for producing such compounds are also disclosed.

22 Claims, 8 Drawing Sheets
Specification includes a Sequence Listing.

(56) References Cited

OTHER PUBLICATIONS

Thompson et al., "Tyrosine sulfation modulates activity of tick-derived thrombin inhibitors", *Nature Chemistry*, 9(9)909-917, 2017.
Figueiredo et al., "Unique thrombin inhibition mechanism by anopheline, an anticoagulant from the malaria vector," *PNAS*, 109(52):E3649-E3658, 2012.
Office Communication issued in Japanese Patent Application No. 2019-531876, dated Aug. 4, 2020. (English translation).
Huntington, "Natural inhibitors of thrombin," *Thrombosis and Haemostasis*, 111(04):583-589, 2014.
Office Communication issued in New Zealand Patent Application No. 754781, dated Feb. 24, 2021.

* cited by examiner

| $A^{Aa}$ | Ki (thrombin) |
|---|---|
| $A^{Aa}$ | 51 ± 0.8 pM |
| $A^{Aa}$(sTyr12) | 6.6 ± 0.5 pM |
| $A^{Aa}$(sTyr34) | 3.1 ± 0.4 pM |
| $A^{Aa}$(sTyr12,34) | 0.68 ± 0.2 pM |

THROMBIN INHIBITORS FOR TREATMENT OF STROKE AND RELATED COAGULATIVE DISORDERS

This application is a national phase application under 35 U.S.C. § 371 of International Application No. PCT/AU2017/051405, filed Dec. 15, 2017, which claims the benefit of Australian Patent Application No. 2016905231, filed Dec. 16, 2016, the entirety of each referenced disclosure is incorporated herein by reference.

Pursuant to 37 C.F.R. 1.821(c), a sequence listing is submitted herewith as an ASCII compliant text file named "FPAPP0008US_ST25.txt", created on Oct. 14, 2019 and having a size of ~15 kilobytes. The content of the aforementioned file is hereby incorporated by reference in its entirety.

FIELD OF THE INVENTION

The invention relates to the treatment of stroke and related diseases, to fibrin clot formation and related thrombin activity, and to preparation of compounds, in particular, peptides and polypeptides for inhibiting, or for modifying the cleavage of fibrinogen by thrombin.

BACKGROUND OF THE INVENTION

Reference to any prior art in the specification is not, and should not be taken as, an acknowledgment or any form of suggestion that this prior art forms part of the common general knowledge in Australia or any other jurisdiction.

Ischaemic stroke is caused by the development of a blood clot or embolus within the cerebral circulation and is the third most common cause of death globally (World Health Organization, 2014). Stroke events are also the leading cause of disability worldwide and are associated with long, resource intensive and costly rehabilitation programs (World Health Organization, 2014).

Currently the only approved pharmacological therapy for stroke to promote the rapid reperfusion of the ischaemic brain, thereby minimising a stroke event, is the intravenous (i.v.) delivery of the thrombolytic agent recombinant tissue plasminogen activator (tPA).

tPA activates plasminogen to plasmin which subsequently degrades fibrin and other clot-associated proteins, thereby improving blood flow through the affected vessel (Wardlaw J M, et al., 2012).

Despite its widespread clinical use, tPA-based therapy has a number of limitations in both efficacy and application. Of particular concern is that only 20-30% of patients will have complete artery re-canalisation following tPA therapy and 20-30% of these patients will experience re-occlusion (Alexandrov A V, Grotta J C., 2002; Rubiera M, et al., 2005). This problem is believed to arise from clot-associated thrombin which retains activity for cleavage of fibrinogen to fibrin as tPA derived plasmin degrades fibrin in the clot.

A further concern is the observation of increased incidence of intracranial haemorrhage (ICH) associated with tPA therapy which effectively limits the dose of tPA that can be given for thrombolytic therapy (Molina C A, Saver J L., 2005).

The significant limitations of tPA therapy have sparked renewed interest in the development of improved thrombolytic therapies.

Thrombin plays a central role in clot formation, principally via the production of insoluble fibrin. As such, thrombin inhibitors have emerged as promising candidates for use as an adjunct therapy with tPA.

To date, the indirect thrombin inhibitor heparin (Von Kummer R 2004; Jang I-K 1999) and the direct thrombin inhibitors (DTIs) hirudin (Karabiyikoglu M 2004) and argatroban (Barreto A D 2012), have been investigated. Whilst an overall improvement in vessel re-canalisation was observed, the risk of bleeding and symptomatic ICH was increased with these co-therapies.

There is a need for thrombin inhibitors that can be used to improve ischaemic stroke outcomes.

There is also a need for thrombin inhibitors that can be used in conjunction with tPA to improve ischaemic stroke outcomes.

There is also a need for thrombin inhibitors that can be used to improve other thrombogenic disease or coagulative disorders.

SUMMARY OF THE INVENTION

The invention seeks to address one or more of the above mentioned needs or limitations and in one embodiment provides a peptide comprising an amino acid sequence shown in

```
SEQ ID No: 1:
PXYXXXZZPXYZZZ
``` or an amino acid sequence shown in

```
                                    SEQ ID No: 2:
            ZXZYZXYDZXXX
``` wherein
Z is D, E, Q, S or P and
X is any amino acid.

The peptide may consist of an amino acid sequence shown in SEQ ID No: 1 or SEQ ID No: 2.

Preferably the peptide binds to exosite II of thrombin.

More preferably the peptide competitively inhibits the binding of clot-associated fibrin, preferably fibrinogen γ', to exosite II of thrombin.

In one embodiment, the peptide may inhibit the binding of a compound selected from the group consisting of Factor V, Factor VIII, Gp1bα, chondroitin sulphate and heparin, to exosite II of thrombin.

Typically at least one residue of the peptide is a sulphated tyrosine residue.

Preferably the tyrosine at position 11 in SEQ ID No: 1 is sulphated. The tyrosine at position 3 in SEQ ID No: 1 may not be sulphated.

Preferably the tyrosine at position 4 in SEQ ID No: 2 is sulphated. The tyrosine at position 7 in SEQ ID No: 2 may not be sulphated.

Preferably the tyrosine at position 7 in SEQ ID No: 2 is sulphated. The tyrosine at position 4 in SEQ ID No: 2 may not be sulphated.

In another embodiment, the tyrosine at position 11 in SEQ ID No: 1 is sulphated and the tyrosine at position 3 is sulphated.

In another embodiment, the tyrosine at position 4 in SEQ ID No: 2 is sulphated and the tyrosine at position 7 is sulphated.

In another embodiment there is provided a thrombin inhibitor of Formula 1:

A-B wherein:

A is a peptide having a sequence shown in SEQ ID No: 1 or SEQ ID No: 2 and has one or more binding characteristics described above;

B is a peptide having a sequence shown in

```
SEQ ID No: 15:
LTYTD
or

SEQ ID No: 16:
VVYTD
or

SEQ ID No: 17:
DPGRRLGE
or

SEQ ID No: 18:
VAEPKM
or

SEQ ID No: 19:
EIPGIR
or

SEQ ID No: 20:
PTAKPR
or

SEQ ID No: 21:
RALHVK
or

SEQ ID No: 22:
EPAKPR
or

SEQ ID No: 23:
PRGGPK
or

SEQ ID No: 24:
TLISAR
``` for binding to the thrombin active site to prevent the thrombin active site from cleaving fibrinogen to form fibrin;

wherein A and B are linked so as to enable A to bind to exosite II of thrombin when B is bound to the thrombin active site.

Region A may be located N terminal to B. In another embodiment, B is located N terminal to A.

In another embodiment there is provided a thrombin inhibitor of Formula 2:

A-α-C wherein:

A is a peptide having a sequence shown in SEQ ID No: 1 or SEQ ID No: 2 and has one or more binding characteristics described above;

B is a peptide having a sequence shown in one of SEQ ID No: 15 to 24 for binding to the thrombin active site to prevent the thrombin active site from cleaving fibrinogen to form fibrin;

C is a peptide having a sequence shown in

```
SEQ ID No: 25:
DFEEIPEEYLQ
or

SEQ ID No: 26:
EDYAAIEASLSETF
or

SEQ ID No: 27:
PFDFEAIPEEYLDDES
``` for binding to exosite I of thrombin;

wherein A, B and C are linked so as to enable A to bind to exosite II of thrombin when B is bound to the thrombin active site and C is bound to exosite I of thrombin.

Region A may be located N terminal to C. In another embodiment, C is located N terminal to A.

In another embodiment there is provided a thrombin inhibitor of Formula 3:

A-C-α wherein:

A is a peptide having a sequence shown in SEQ ID No: 1 or SEQ ID No: 2 and has one or more binding characteristics described above;

B is a peptide having a sequence in one of SEQ ID No: 15 to 24 for binding to the thrombin active site to prevent the thrombin active site from cleaving fibrinogen to form fibrin;

C is a peptide having a sequence shown in in one of SEQ ID No: 25 to 27 for binding to exosite I of thrombin;

wherein A, B and C are linked so as to enable A to bind to exosite II of thrombin when B is bound to the thrombin active site and C is bound to exosite I of thrombin.

Region A may be located N terminal to B. In another embodiment, B is located N terminal to A.

In another embodiment there is provided a thrombin inhibitor of Formula 4:

B-A-C wherein:

A is a peptide having a sequence shown in SEQ ID No: 1 or SEQ ID No: 2 and has one or more binding characteristics described above;

B is a peptide having a sequence shown in one of SEQ ID No: 15 to 24 for binding to the thrombin active site to prevent the thrombin active site from cleaving fibrinogen to form fibrin;

C is a peptide having a sequence shown in one of SEQ ID No: 25 to 27 for binding to exosite I of thrombin;

wherein A, B and C are linked so as to enable A to bind to exosite II of thrombin when B is bound to the thrombin active site and C is bound to exosite I of thrombin.

Region B may be located N terminal to C. In another embodiment, C is located N terminal to B.

In one embodiment, a peptide of Formula 1 or Formula 2 or Formula 3 or Formula 4 provides for a clotting time that is at least 20% shorter than hirudin on a molar equivalent basis of the peptide and hirudin.

Preferably, a peptide of Formula 1 or Formula 2 or Formula 3 or Formula 4 provides for a bleeding time that is at least 20% shorter than hirudin on a molar equivalent basis of the peptide and hirudin.

In another embodiment there is provided a pharmaceutical composition including a peptide of SEQ ID No: 1 or SEQ ID No: 2 as generally described above, or a peptide of Formula 1 or Formula 2 or Formula 3 or Formula 4 described above and a pharmaceutically effective carrier, diluent or excipient.

In another embodiment there is provided a nucleic acid, preferably cDNA, having a nucleotide sequence encoding a peptide of SEQ ID No: 1 or SEQ ID No: 2 as generally described above, or a peptide of Formula 1 or Formula 2 or Formula 3 or Formula 4 described above, and vectors, expression constructs and cells containing said nucleic acid.

Preferably the cell contains a sulfotransferase enabling sulphation of tyrosine.

In one embodiment, a sulfotyrosine is genetically incorporated into a peptide according to the invention by amber codon suppression.

In another embodiment there is provided a peptide of SEQ ID No: 1 or SEQ ID No: 2 as generally described above, or a peptide of Formula 1 or Formula 2 or Formula 3 or Formula 4 described above, or pharmaceutical composition described above, for use in a thrombolytic therapy.

Preferably the thrombolytic therapy includes tPA therapy.

More preferably the thrombolytic therapy is for minimisation of an ischaemic stroke outcome.

DETAILED DESCRIPTION OF THE EMBODIMENTS

Figures 1A, 1B:
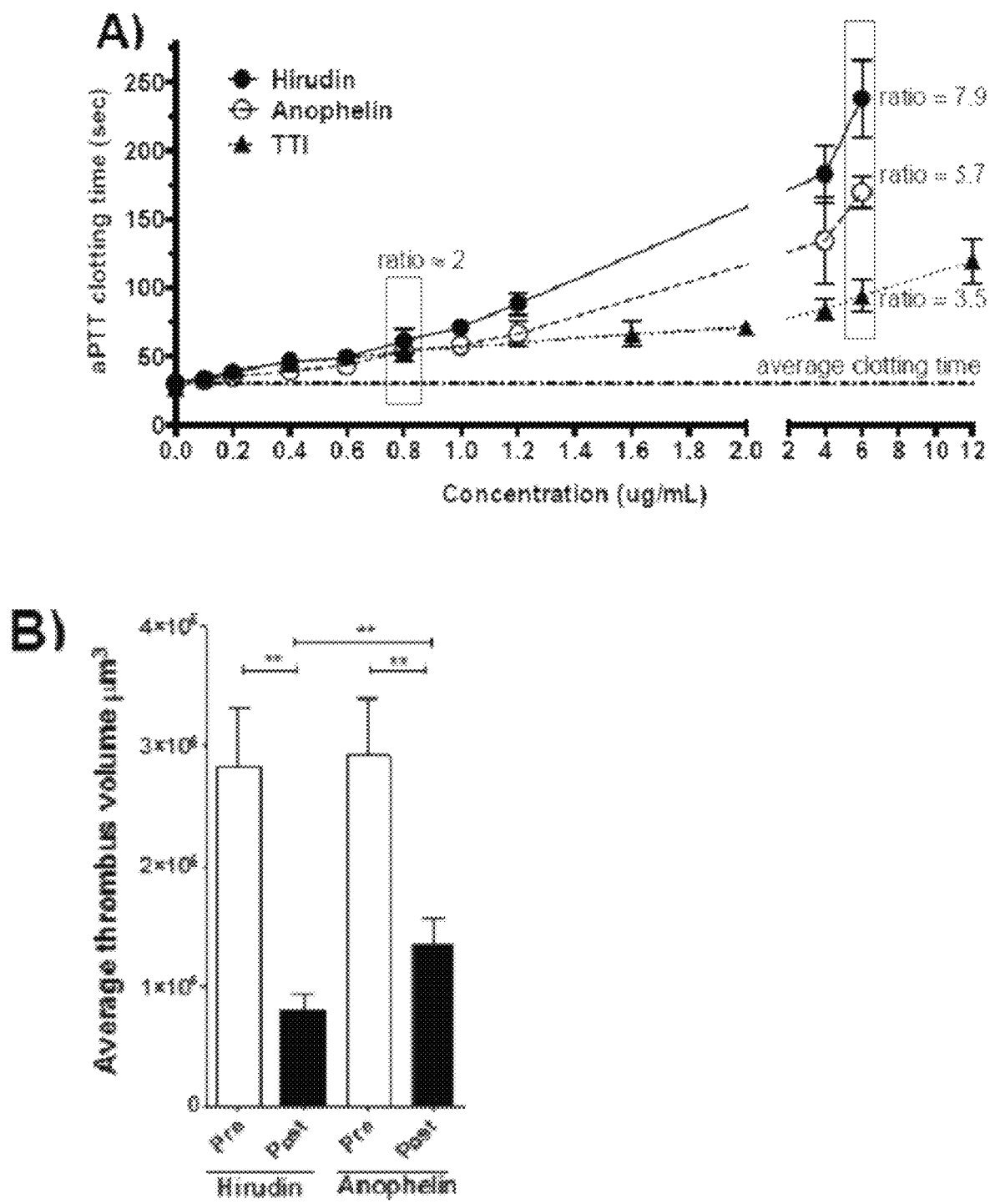
FIG. 1. Sulfated thrombin inhibitors possess potent in vivo anticoagulant activity. a) in vitro APTT assay with varying concentrations of hirudin, and doubly sulfated thrombin inhibitors; b) reduced thrombus volume after administration of hirudin and sulfated thrombin inhibitors (both 1 mg/kg; i.v.); c) bleeding times following equimolar delivery of hirudin (0.5 mg/kg), and sulfated thrombin inhibitor peptide (0.5 mg/kg) in a tail bleed model; d) reduced fibrin after administration of hirudin and sulfated thrombin inhibitors (both 1 mg/kg; i.v.) following needle injury to the vessel; e) representative confocal images showing reduction of platelet thrombus (red) and fibrin (yellow) by administration of hirudin (1 mg/kg; i.v.) and sulfated thrombin inhibitor (1 mg/kg, i.v.) after needle injury to the vessel.

The invention is particularly concerned with inhibiting the binding of endogenous components of the coagulation cascade to exosite II of thrombin. Disclosed herein are peptides that bind to thrombin exosite II and that competitively inhibit some of these components.

It is proposed that these peptide inhibitors may be utilised to inhibit fibrin formation by clot-associated thrombin, thereby addressing some of the issues regarding re-canalisation associated with tPA therapy. The peptide inhibitors may also be used to modify the binding affinity and/or function of other peptides that bind to and block function of the thrombin active site, or the thrombin exosite I.

A. Definitions

"Thrombin" is a serine protease having a central role in hemostasis through the conversion of fibrinogen to fibrin.

"Thrombin active site" is a catalytic site that cleaves a range of substrates including fibrinogen, fibrinopeptides, Factor V, Factor VIII, protease activated receptors (PARs), glycoprotein V, Factor XI, Factor XIII, ADAMTS13, protein C.

"Thrombin exosite II", (also known as "heparin binding exosite") is a positively charged recognition surface that influences substrate and cofactor binding, particularly fibrinogen, Gp1bα, and heparin. It may include residues R93, R101, R126, K236, K240, and R233.

"Thrombin exosite I" (also known as "fibrinogen binding exosite") is a positively charged recognition surface that influences substrate and cofactor binding, particularly fibrinogen, Factor V, Factor VIII, ADAMTS13, Factor XIII, PAR-1, Factor XI and thrombomodulin. It may include residues K36, H71 R73, R75, Y76, and R77.

Thrombin, including the thrombin active site and exosites I and II are generally discussed in Lane D. et al. 2005 Blood J. 106:2605-2612.

"sulphated tyrosine residue" and "tyrosine-O-sulfate" is a residue arising from the transfer of a sulfur-containing group to the hydroxyl side chain of tyrosine. The residue may arise from the action of a tyrosylprotein sulfotransferase (TPST).

"bleeding time" generally refers to the time required for bleeding to stop. It has been utilised clinically to assess platelet function. A range of assays for assessing bleeding time are known in the art: See in general Greene T. K. et al. 2010 J. Thromb and Haem 8:2820-2822; Liu Y., et al. 2012 WJEM 2: 30-36; Broze G. J. et. al 2001 Thromb Haemost 85:747-748.

"clotting time" generally refers to the time required for formation of a fibrin clot. Typically clotting time is assessed by the activated partial thromboplastin time (APTT) test.

"Hirudin" is a low molecular weight peptide (7 kDa) comprised of 65 amino acids (Dodt et al., 1984 FEBS Lett., 165: 180-4) which prevents blood from coagulating by binding to exosite I and the thrombin active site (Stone and Hofsteenge, 1986 Biochem, 25:4622-28).

"Comprise" and variations of the term, such as "comprising", "comprises" and "comprised", are not intended to exclude further additives, components, integers or steps.

B. Exosite II Inhibitors

In one embodiment there is provided a peptide comprising, or consisting of an amino acid sequence shown in SEQ ID No: 1
PXYXXXZZPXYZZZ wherein
Z is D or E and
X is any amino acid.
The peptide may have a sequence as shown in:

SEQ ID No: 3
(PBYXXGZZPXYZZZ wherein Z is D/E and B is K/R/H and X is any amino acid.)

SEQ ID No: 4
(PQYJXGZZPOYZZZ wherein Z is D/E and J is A/T/S or G and O is S or T and X is any amino acid.)

SEQ ID No: 5
(PQYAXGZZPOYZZZ wherein Z is D/E and O is S/T and X is any amino acid.)

SEQ ID No: 6
(PQYAXGZZPOYZZZXXXXZXX wherein Z is D/E and O is S/T and X is any amino acid.)

SEQ ID No: 7
(PQYAXGZZPOYZZZ(D/T)(D/G/F)(D/A)(S/D/E)(D/E)(K/P/S)(L/V) wherein Z is D/E and O is S/T and X is any amino acid.)

SEQ ID No: 8
(PQYAXGZZPOYZZZDDDDD(K/P/S)(L/V) wherein Z is D/E and O is S/T and X is any amino acid.)

SEQ ID No: 9
(PQYAXGZZPOYZZZDDDEE(K/P/S)(L/V) wherein Z is D/E and O is S/T and X is any amino acid.)

SEQ ID No: 10
(PQYAPGDEPSYDED)

SEQ ID No: 11
(PQYAPGEEPSYDED)

SEQ ID No: 12
(PQYTHGEEPEYDED)

SEQ ID No: 13
(PQYAQGEEPTYDED)

SEQ ID No: 14
(PQYARGDVPTYDEE)

In another embodiment there is provided a peptide comprising, or consisting of an amino acid sequence shown in SEQ ID No: 2:
ZXZYZXYZXXX wherein
Z is D, E, Q, S or P and
X is any amino acid.
The peptide may have a sequence as shown in:

SEQ ID No: 28
(DADYDEYEEDG)

SEQ ID No: 29
(DGDYDEYDNDE)

SEQ ID No: 30
(QGDYDEYDQDE)

SEQ ID No: 31
(DADYDDYDEEG)

SEQ ID No: 32
(DVSYDEYEDNG)

SEQ ID No: 33
(QDDYDEYDADE)

SEQ ID No: 34
(ETDYDEYEENE)

SEQ ID No: 35
(ESDYDTYPDDN)

SEQ ID No: 36
(DDEYDMYESDG)

SEQ ID No: 37
(ETSYEEYPDDS)

SEQ ID No: 38
(ESDYDTYPDDN)

SEQ ID No: 39
(ERDDEDYDNSN)

SEQ ID No: 40
(ZXZYZZYZZZZ wherein Z is D/E and X is T/M/E/S/D/G/N/P)

SEQ ID No: 41
ZSZYZTYPDDN wherein Z is D/E)

SEQ ID No: 42
ZDZYZMYESDG wherein Z is D/E)

SEQ ID No: 43
ZTSYZEYPDDS wherein Z is D/E)

SEQ ID No: 44
ZSZYZTYPDDN wherein Z is D/E)

In one embodiment the peptide consists of no more than about 35 amino acids, preferably about 30 to 35 amino acids, more preferably about 30, 31, 32, 33, 34 or 35 amino acids.

Preferably the peptide binds to exosite II of thrombin.

The peptide may competitively inhibit the binding of clot-associated fibrin, preferably fibrinogen γ', to exosite II of thrombin. The peptide may have a higher affinity for exosite II of thrombin than does fibrinogen γ'. This would enable the peptide to ostensibly elute clot-associated thrombin from a clot the subject of tPA thrombolytic therapy, thereby minimising the incidence of reduced re-canalisation that is otherwise associated with tPA therapy.

In one embodiment, the peptide may inhibit the binding of a compound selected from the group consisting of Factor V, Factor VIII, Gp1bα, chondroitin sulphate and heparin, to exosite II of thrombin.

Typically at least one residue of the peptide is a sulphated tyrosine residue.

Preferably the tyrosine at position 11 in SEQ ID No: 1 is sulphated. The tyrosine at position 3 in SEQ ID No: 1 may not be sulphated.

In another embodiment, the tyrosine at position 11 in SEQ ID No: 1 is sulphated and the tyrosine at position 3 is sulphated.

As described in the Examples herein, the sulfation of either or both tyrosine residues is associated with improvements in inhibition of thrombin activity.

Preferably the tyrosine at position 4 in SEQ ID No: 2 is sulphated. The tyrosine at position 7 in SEQ ID No: 2 may not be sulphated.

Preferably the tyrosine at position 7 in SEQ ID No: 2 is sulphated. The tyrosine at position 4 in SEQ ID No: 2 may not be sulphated.

In another embodiment, the tyrosine at position 4 in SEQ ID No: 2 is sulphated and the tyrosine at position 7 is sulphated.

Sulfation of tyrosine residues can be achieved by expressing a nucleic acid encoding a peptide of SEQ ID No: 1 or SEQ ID No: 2 in a cell that contains a tyrosylprotein sulfotransferase (TPST). In more detail, inorganic sulfate may be actived in the forms of adenosine-5'-phosphosulfate (APS) and 3'-phospho-adenosine-5'-phosphosulfate (PAPS) by ATP sulfurylase and APS kinase respectively. The activated sulfate may then be transferred to tyrosine by TPST in the Golgi body.

Another approach to obtain sulphated tyrosine residues in a peptide according to the invention is to utilise a recombinant expression system involving an amber codon suppression enabling sulfotyrosine to be incorporated into the peptide during the recombinant synthesis of the peptide.

In the Examples herein, the inventors provide a synthetic method enabling the production of homogenous compositions of sulphated peptides (i.e. compositions that contain a peptide having only one sulfation profile).

The exosite II inhibitors described herein may be tested for specificity for binding to thrombin exosite II by utilising a thrombin/γ'peptide binding assay as described in Lovely R S et al. 2002. Briefly, an exosite II inhibitor or binder, or putative exosite II inhibitor or binder is labelled, incubated with thrombin and fluorescence polarization is measured. The assay can be used in a competitive inhibitor model to enable the determination of inhibition constants for each exosite II binding peptide.

As described above, at least 20-30% of patients who receive tPA therapy for ischaemic stroke will have complete artery re-canalisation following tPA therapy and of these, 20-30% will experience re-occlusion. Some consider that this arises when tPA therapy reveals clot-entrapped thrombin which is understood to be bound to the clot via exosite II, enabling the active site of the thrombin to cleave fibrinogen and fibrinopeptides to amplify and build the clot. Exosite II inhibitors described herein are provided to an individual receiving tPA therapy to enable the elution of clot-associated thrombin from a fibrin clot, thereby minimising the amount of thrombin at the clot which would otherwise cause fibrin production and clot expansion.

Thus, in one embodiment there is provided, in a method of tPA therapy, the step of providing an exosite II inhibitor of thrombin described herein in a therapeutically effective amount.

Typically the exosite II inhibitor of thrombin is provided in the form of a composition adapted for i.v. administration.

Typically the exosite II inhibitor of thrombin is provided in an amount of about 100 µg/kg to 10 mg/kg of the recipient.

C. Thrombin Inhibitors

In further embodiments the invention relates to utilising the exosite II binding peptides disclosed herein for design, modification and/or production of novel inhibitors of thrombin activity, in particular for inhibitors that prevent or at least minimise the cleavage of fibrinogen or fibrinopeptides by thrombin. These exosite II binding peptides may provide for inhibitors that have an improved affinity for the binding to the thrombin active site, and/or to exosite I.

A thrombin inhibitor may be described according to Formula 1:

A-B wherein:
A is an exosite II binding peptide having a sequence shown in SEQ ID No: 1 or SEQ ID No: 2 and as generally described above;
B is a peptide having a sequence shown in one of SEQ ID No: 15 to 24 for binding to the thrombin active site to prevent the thrombin active site from cleaving fibrinogen to form fibrin;
wherein A and B are linked so as to enable A to bind to exosite II of thrombin when B is bound to the thrombin active site.

It will be understood that A may be located N terminal to B, or alternatively, B may be located N terminal to A.

In a further embodiment, a thrombin inhibitor may be described according to Formula 2:

A-B—C wherein:
A is an exosite II-binding peptide having a sequence shown in SEQ ID No: 1 or SEQ ID No: 2 and as generally described above;
B is a peptide having a sequence shown in one of SEQ ID No: 15 to 24 for binding to the thrombin active site to prevent the thrombin active site from cleaving fibrinogen to form fibrin;
C is a peptide having a sequence shown in one of SEQ ID No: 25 to 27 for binding to exosite I of thrombin;
wherein A, B and C are linked so as to enable A to bind to exosite II of thrombin when B is bound to the thrombin active site and C is bound to exosite I of thrombin.

It will be understood that the A may be located N terminal to C, or alternatively, C may be located N terminal to A.

In yet a further embodiment a thrombin inhibitor may be described according to Formula 3:

A-C—B wherein:
A is an exosite II binding peptide having a sequence shown in SEQ ID No: 1 or SEQ ID No: 2 and as generally described above;
B is a peptide having a sequence shown in one of SEQ ID No: 15 to 24 for binding to the thrombin active site to prevent the thrombin active site from cleaving fibrinogen to form fibrin;
C is a peptide having a sequence shown in one of SEQ ID No: 25 to 27 for binding to exosite I of thrombin;
wherein A, B and C are linked so as to enable A to bind to exosite II of thrombin when B is bound to the thrombin active site and C is bound to exosite I of thrombin.

It will be understood that A may be located N terminal to B, or alternatively, B may be located N terminal to A.

In yet a further embodiment, a thrombin inhibitor may be described according to Formula 4:

B-A-C wherein:
A is an exosite II binding peptide having a sequence shown in SEQ ID No: 1 or SEQ ID No: 2 and as generally described above;

B is a peptide having a sequence shown in one of SEQ ID No: 15 to 24 for binding to the thrombin active site to prevent the thrombin active site from cleaving fibrinogen to form fibrin;

C is a peptide having a sequence shown in one of SEQ ID No: 25 to 27 for binding to exosite I of thrombin;

wherein A, B and C are linked so as to enable A to bind to exosite II of thrombin when B is bound to the thrombin active site and C is bound to exosite I of thrombin.

It will be understood that B may be located N terminal to C, or alternatively, C may be located N terminal to B.

The thrombin inhibitors of Formula 1 to 4 may include a linker in the form of a peptide sequence (for example a peptide including 2 or more amino acid residues such as Gly and Ala) or other polymer (for example, a diethylene glycol linker) that links B (active site binding peptide) with A (exosite II binding peptide); or B (active site binding peptide) with C (exosite I binding peptide); or A (exosite II binding peptide) with C (exosite I binding peptide). Examples of peptide sequences include poly Ala or poly Gly peptides. The length of the linker peptides may be determined according to the molecular distance between the relevant thrombin sites. These molecular distances are as follows: (i) thrombin active site to exosite II: 38 to 60 angstroms; (ii) thrombin active site to exosite I: 27 to 40 angstroms; (iii) exosite II to exosite I: 65 to 100 angstroms.

The above described inhibitors may be prepared by solid phase peptide synthesis. For example, an inhibitor of Formula 1 may be prepared by a method including the steps of solid phase synthesis of A, selective desulfurisation of A so as to retain a desired tyrosine sulfation profile, solid phase synthesis of B, and ligation of A to B, or as an alternative in the final step, ligation of A to a linker, and ligation of the A-linker conjugate to B to from an A linker-B conjugate.

In other embodiments, the inhibitors may be synthesised by recombinant DNA technology. It is particularly preferred that the cell lines used in this technology are (i) capable of growing in the presence of inorganic sulfate and (ii) capable of assimilating inorganic sulfate into a biological system, in particular a system involving post translational modification of tyrosine residues. Such a cell line generally includes a tyrosylprotein sulfotransferase in the Golgi body, enabling the formation of one or more tyrosine-O-sulfate residues. In certain embodiments the expression products may be heterogeneous with respect to tyrosine sulfation pattern. A homogenous population of tyrosine-sulfated isoforms can be obtained by purifying the expression products on a variety of separation systems including a chromatographic system enabling differentiation of isoforms on the basis of tyrosine-sulfated phenotype.

Inhibitors described herein may be investigated for thrombin selectivity by counter-screening against a panel of proteases including trypsin, chymotrypsin, elastase, papain, reptilase, and factor Xa and activated protein C from the blood coagulation cascade. Inhibitors are screened initially at a single concentration (5 µM) using a fluorescence polarisation assay as described above.

Molecular details of thrombin recognition and inhibition by the inhibitors described herein may be determined by solving the three-dimensional structures of their complexes with thrombin. Briefly, thrombin-inhibitor complexes are prepared in vitro and subjected to extensive sub-microlitre scale screenings for crystallisation conditions. Preliminary conditions are refined and optimised using custom grid screens. Determination of cryoprotection conditions and initial sample characterisation is performed using a X-ray diffractometer. High resolution X-ray diffraction data is collected at high brilliance synchrotron sources, ensuring an adequate level of detail in the resulting models. The structures are solved by molecular replacement techniques using the coordinates of unliganded human thrombin as search model and refined and interpreted using a computational platform. These data provide detail on the binding mode of the inhibitors and unveil key interactions with thrombin.

The anticoagulant activity of the thrombin inhibitors disclosed herein is determined by measuring their ability to prolong clotting of human plasma in vitro using a clinical TT assay. Briefly, human plasma from healthy donors (800 µL) is mixed with a concentration range of inhibitors, clotting initiated by addition of thrombin, and clotting time measured using a coagulometer. Compounds which prolong clotting time to 30 sec at a concentration of 50 nM may be further investigated in vitro/ex vivo for APTT. In brief, pooled citrated plasma from C57BL6/J mice is pre-incubated with various concentrations (0-12 µg/mL) of inhibitors. APTT of each plasma sample is quantified following addition of a coagulation activator and $CaCl_2$). In an ex vivo assay, mice are injected i.v. with inhibitors (fixed concentration determined from in vitro APTT) and whole blood collected into sodium citrate (~130 µL) 0, 5, 30 and 60 min post-administration. APTT is quantified on isolated plasma using a RANDOX APTT kit, with fibrin generation monitored to measure clotting time.

The inventors show in the Examples that polypeptides having an exosite II binding peptide described above possess potent in vivo antithrombotic activity with reduced clotting time and reduced bleeding time compared to known anticoagulants. This is advantageous because many anti-thrombotic drugs are limited in their use due to risk of bleeding (including intracranial bleeding in stroke therapy).

Bleeding time is an important issue clinically, as bleeding risk is markedly increased in patients receiving anticoagulant therapy. Specifically, there is no effective treatment available against bleeding caused by known anticoagulants including hirudin. There is therefore a need for agents that reduce bleeding time.

The inventors demonstrate the surprising effect that the sulfated polypeptides according to the present invention display significantly less bleeding compared to the known coagulant hirudin.

In one embodiment, the sulfated polypeptides according to the present invention reduce bleeding by more than 2-fold when compared to hirudin. In another embodiment, the sulfated polypeptides according to the present invention reduce bleeding time by more than 3-fold when compared to hirudin. In another embodiment, the bleeding time in the presence of sulfated polypeptides according to the present invention occurs for no longer than 10 minutes.

In another embodiment, the bleeding time in the presence of sulfated polypeptides according to the present invention is reduced by more than 20%, by more than 30%, by more than 40%, by more than 50%, or by more than 60% when compared to hirudin.

The disclosed peptides and compositions can be used for inhibiting thrombin activity, for example in anti-thrombotic amounts sufficient to inhibit thrombin activity in a subject, such as a human, in whom pathological thrombosis is not desired. The compositions can be used in subjects who suffer from a condition such as myocardial infarction, stroke, pulmonary embolism, deep vein thrombosis, peripheral arterial occlusion, disseminated intravascular coagulation, cardiovascular and cerebrovascular thrombosis, thrombosis associated with post-operative trauma, obesity, pregnancy, side effects of oral contraceptives, prolonged immobilization, and hypercoaguable states associated with hematologic, immunologic or rheumatological disorders. Alternatively, the subject may suffer from unstable angina, arteriosclerosis, a reblockage of vessels after angioplasty with a balloon catheter, or blood clotting in hemodialysis.

EXAMPLES

Example 1—Synthesis of Sulfated Exosite II Binders

Fragments of full length thrombin inhibitors that bind only exosite II were synthesised by Fmoc-strategy SPPS.

Resin Loading: 2-Chlorotrityl chloride resin, Rink amide resin or Wang resin was loaded with the C-terminal amino acid of the target sulfopeptide as per the manufacturer's instructions.

Iterative Peptide Assembly (Fmoc-SPPS)

Deprotection: The resin was treated with piperidine/DMF (1:4, v/v, 3 mL, 3×5 min), filtered and then washed with DMF (5×3 mL), $CH_2Cl_2$ (5×3 mL) and DMF (5×3 mL).

Coupling (standard Fmoc-protected amino acids): A solution of a standard Fmoc-protected amino acid (4 equiv.), PyBOP (4 equiv.) and NMM (8 equiv.) in DMF (final concentration 0.1 M) was added to the resin. After 1 h, the resin was filtered and washed with DMF (5×3 mL), $CH_2Cl_2$ (5×3 mL) and DMF (5×3 mL).

Site specific incorporation of tyrosine sulfate: Tyrosine sulfate was incorporated into the desired peptide fragments by one of two methods:
1) Coupling of an amino acid cassette [Fmoc-Tyr($SO_2OCH_2C(CH_3)_3$)—OH]: A solution of Fmoc-Tyr($SO_2OCH_2C(CH_3)_3$)—OH (1.2 equiv.), HATU (1.2 equiv.) and NMM (2.4 equiv.) in DMF (final concentration 0.1 M) was added to the resin. After 18 h, the resin was filtered and washed with DMF (5×3 mL), $CH_2Cl_2$ (5×3 mL) and DMF (5×3 mL).
2) Solid phase sulfation following incorporation of Fmoc-TyrOAll-OH: Solid phase sulfation was carried out with a imidazolium sulfating reagent using the method described in: Taleski, D et al. 2011 or Hsieh, Y. S. et al 2014.

Capping: Acetic anhydride/pyridine (1:9, v/v, 3 mL) was added to the resin. After 3 min the resin was filtered and washed with DMF (5×3 mL), $CH_2Cl_2$ (5×3 mL) and DMF (5×3 mL).

Cleavage: The sulfated peptide was cleaved from the resin with concomitant side chain deprotection using an acidic cleavage cocktail, e.g. 90:5:5 v/v/v trifluoroacetic acid/triisopropylsilane/water.

Deprotection of Sulfate Ester Protecting Groups:
1) Deprotection of the neopentyl sulfate ester (from cassette strategy) was performed by treatment with sodium azide solution or aqueous ammonium acetate as described in Ziarek, J. J et al 2013.
2) Deprotection of the dichlorovinylsulfate esters and trichloroethylsulfate esters (from the solid-phase sulfation strategy) was performed using hydrogenation as described in Taleski, D. et al 2011. Deprotection of trifluoroethylsulfate esters was achieved using aqueous ammonium acetate as described in Hsieh, Y. S. et al. 2014.

Purification: Purification of site specifically sulfated exosite II binding peptide fragments was achieved using reversed-phase HPLC purification.

Example 2—Synthesis of Thrombin Inhibitor of Formula 2 (AAa)

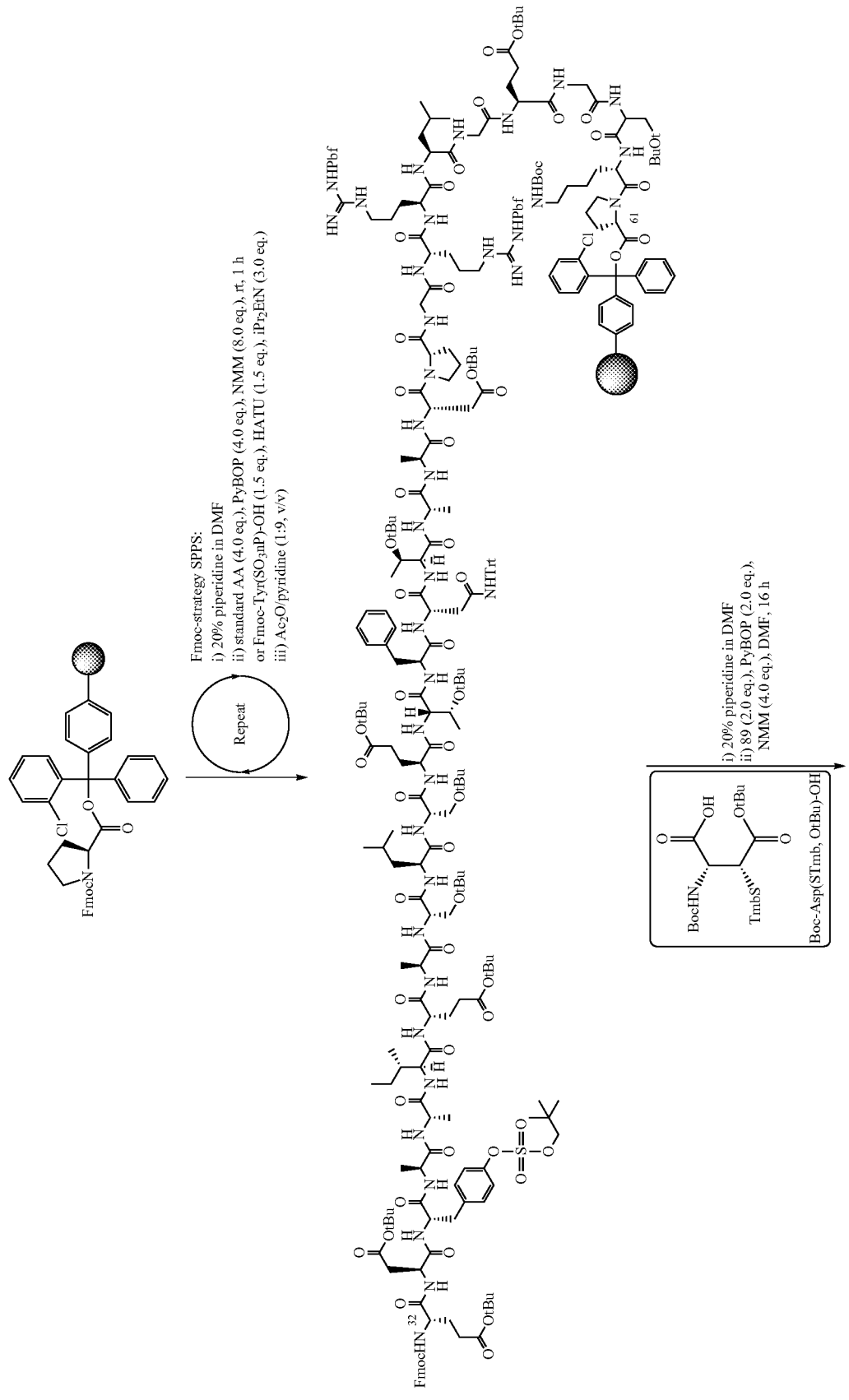

-continued
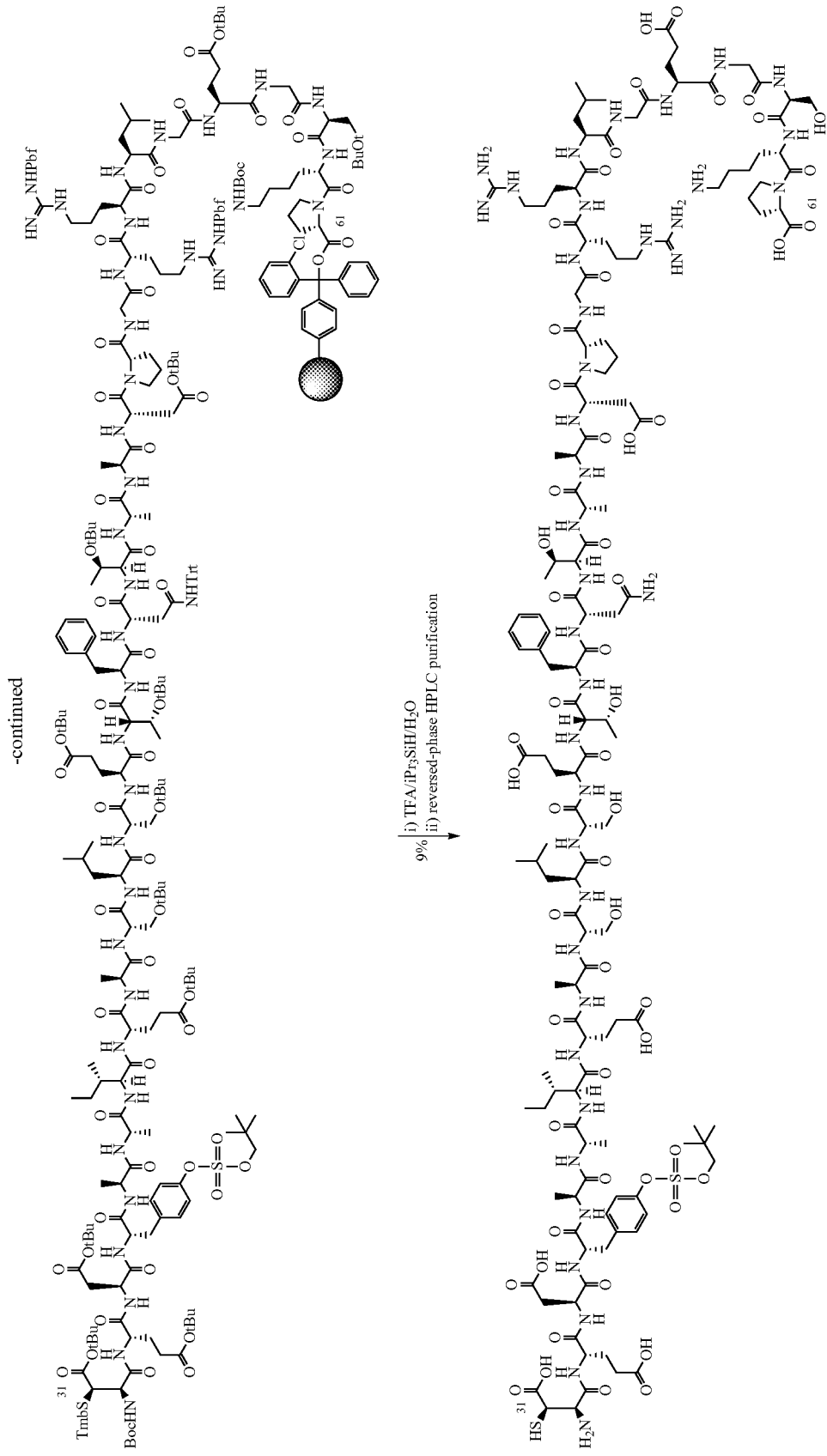

Figures 3A, 3B:
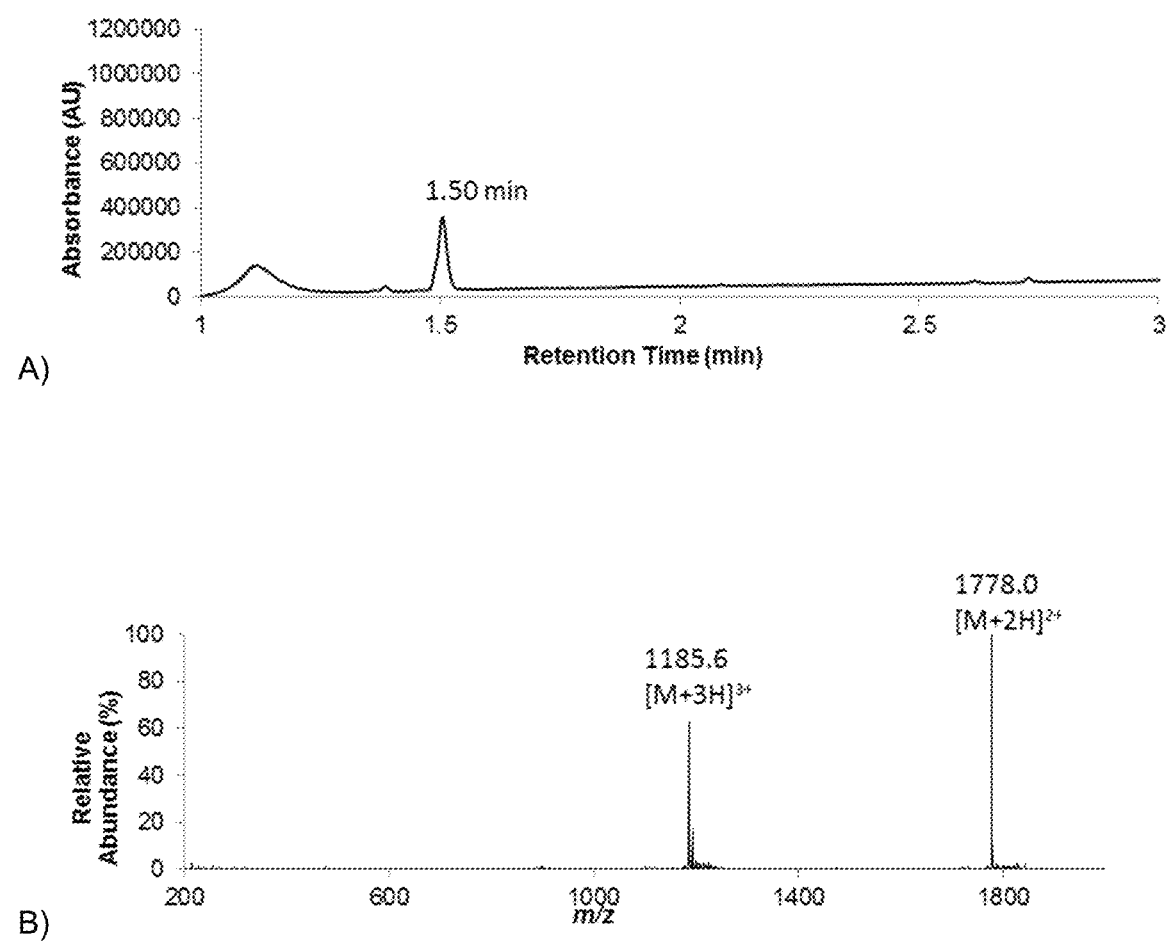
FIG. 3 A) Analytical UPLC of $A^{4a}$ (31-61) fragment 88: $R_t$ 1.50 min (0 to 60% B over 3 min, Eluent B, $\lambda$=230 nm); B) Mass spectrum (ESI+) of 88: Calculated mass for (neutral) $C_{143}H_{225}N_{39}O_{56}S_2$ [M]: 3449.5, $[M+2H]^{2+}$: 1777.7 (100%), $[M+3H]^{3+}$: 1185.5 (100.0%); Mass Found (ESI+) $[M+2H]^{2+}$: 1778.0, $[M+3H]^{3+}$: 1185.6.

Fmoc-Pro-OH (84 mg, 250 μmop was loaded onto CTC resin using standard loading procedure. Iterative Fmoc-SPPS was then carried out as outlined above to give the fully assembled resin bound $A^{Aa}$ (32-61). The peptide on resin was split and 25 μmol peptide was used in the following treatment. The peptide was Fmoc-deprotected with 20% piperidine in DMF (2×5 mL) and Boc-Asp(STmb, OtBu)-OH (25 mg, 50 μmol, 2.0 eq.) was subsequently coupled using PyBOP (26 mg, 50 μmol, 2.0 eq.) and NMM (0.11 mL, 101 mg, 0.10 mmol, 4.0 eq.) in DMF (1.5 mL) at room temperature for 16 h. The resin was washed with DMF (5×5 mL), $CH_2Cl_2$ (5×5 mL) and DMF (5×5 mL). The peptide was deprotected and cleaved from resin using TFA/iPr$_3$SiH/H$_2$O (4 mL, 90:5:5 v/v/v) and the resulting mixture was agitated for 2 h. The crude peptide was precipitated from ice-cold Et$_2$O (20 mL) and purified by reversed-phase preparative HPLC (20 to 80% B over 60 min, Eluent A) to afford the desired peptide 88 as a TFA salt (8.8 mg, 9.0%) after lyophilisation. See FIGS. 3 A&B.

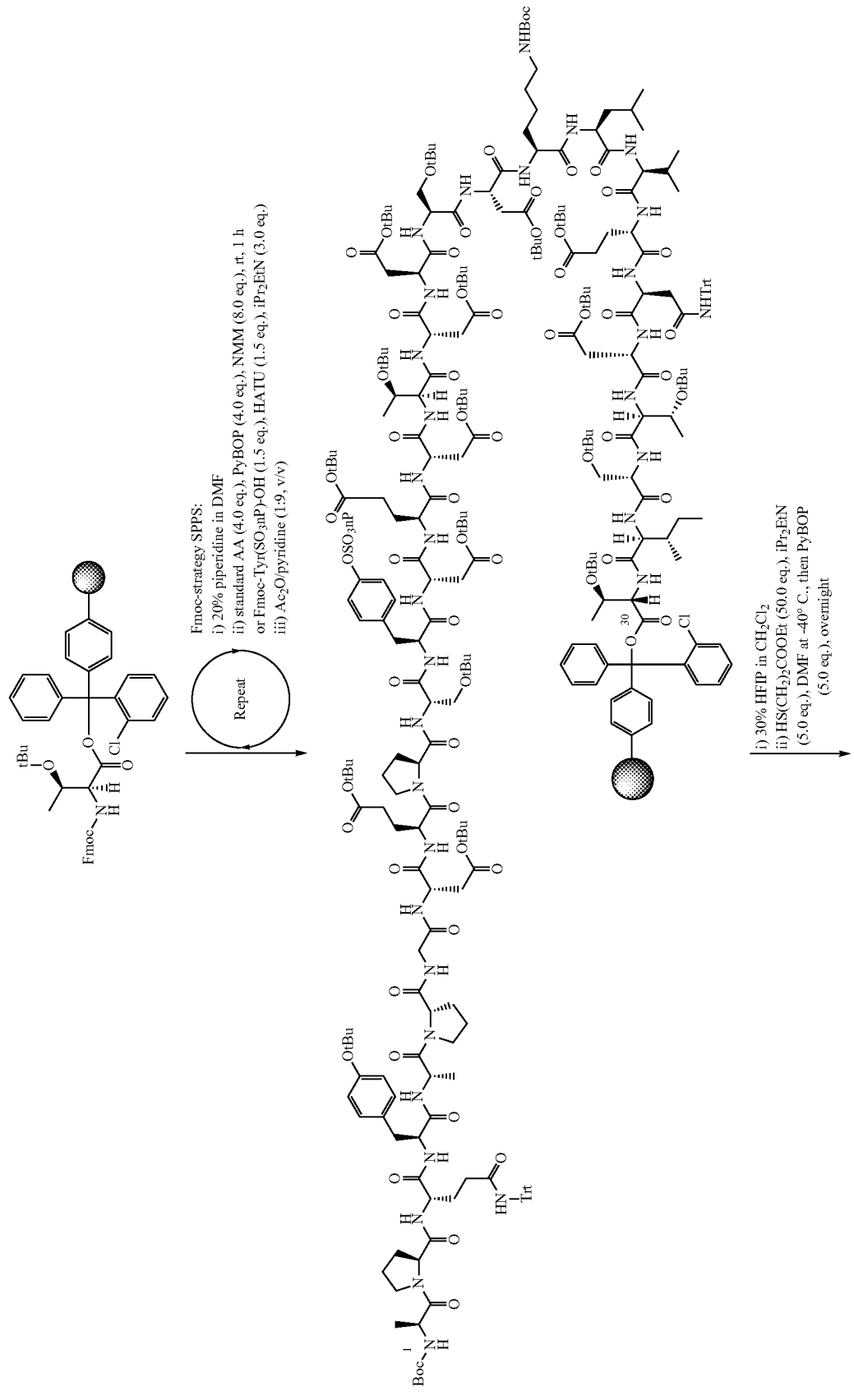

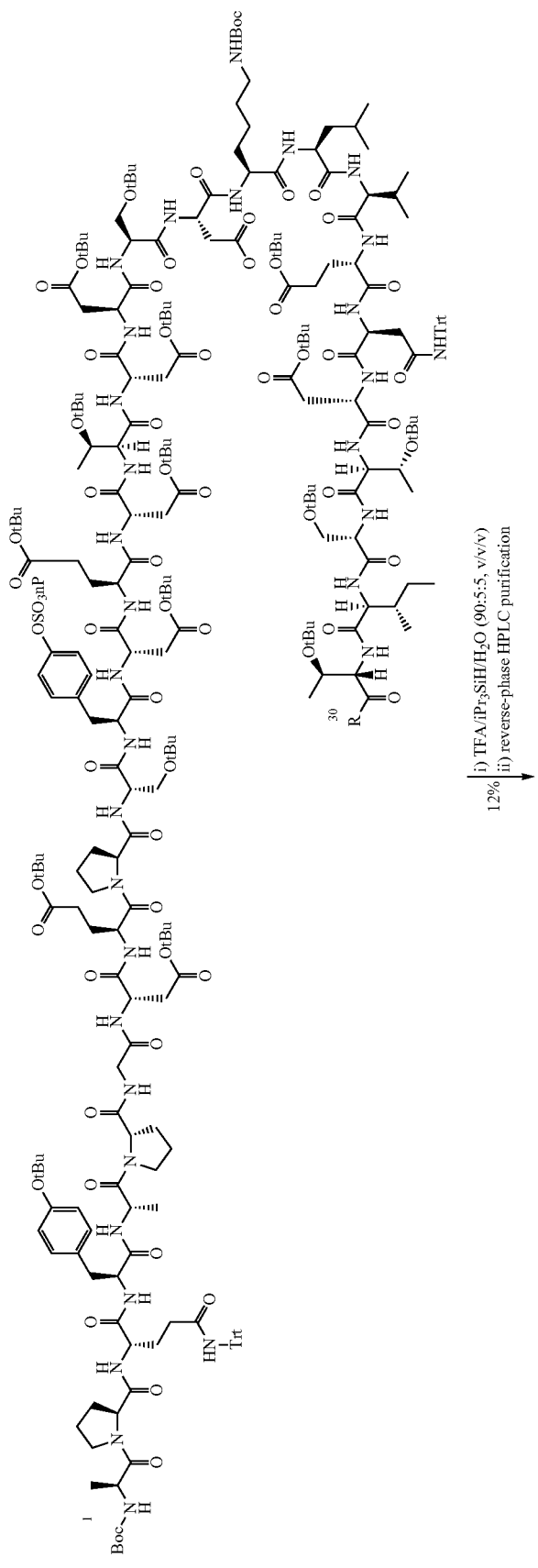

-continued
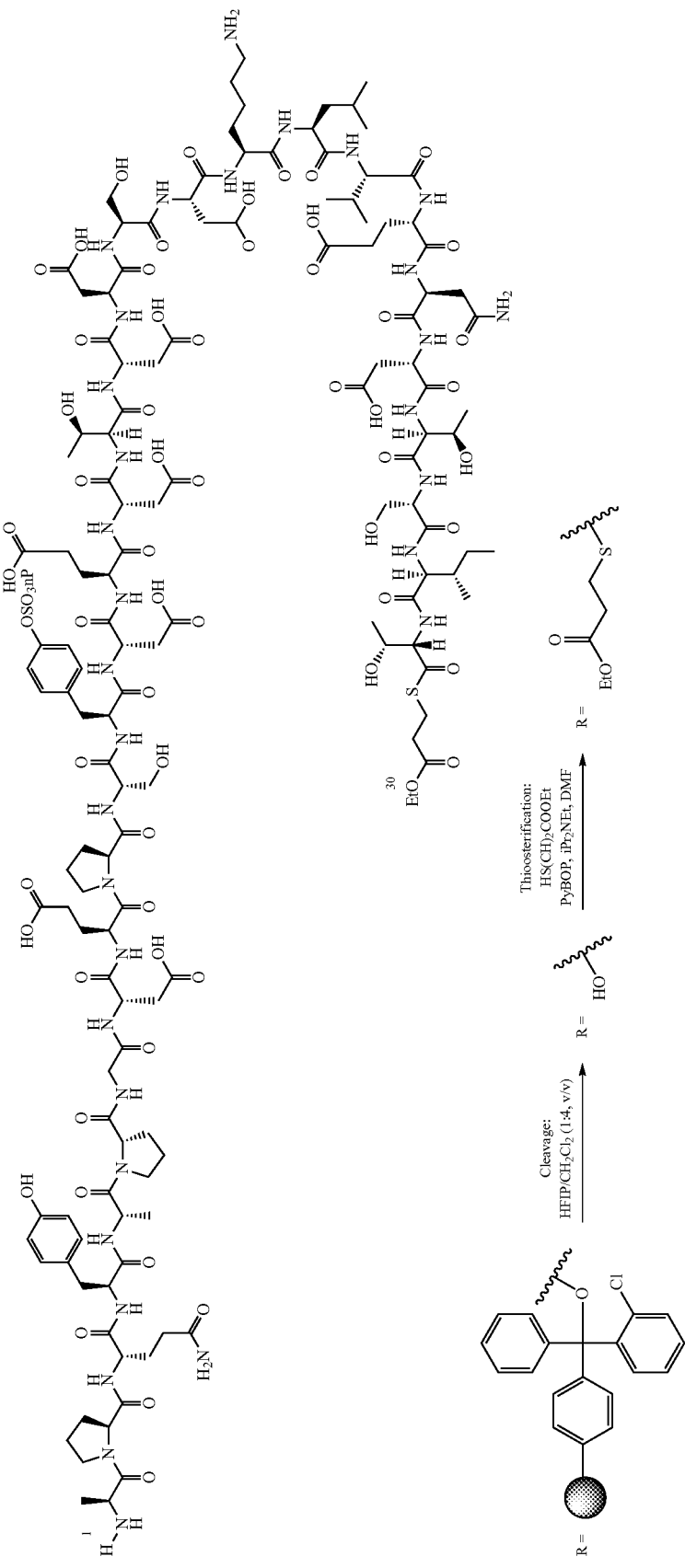

Figures 4A, 4B:
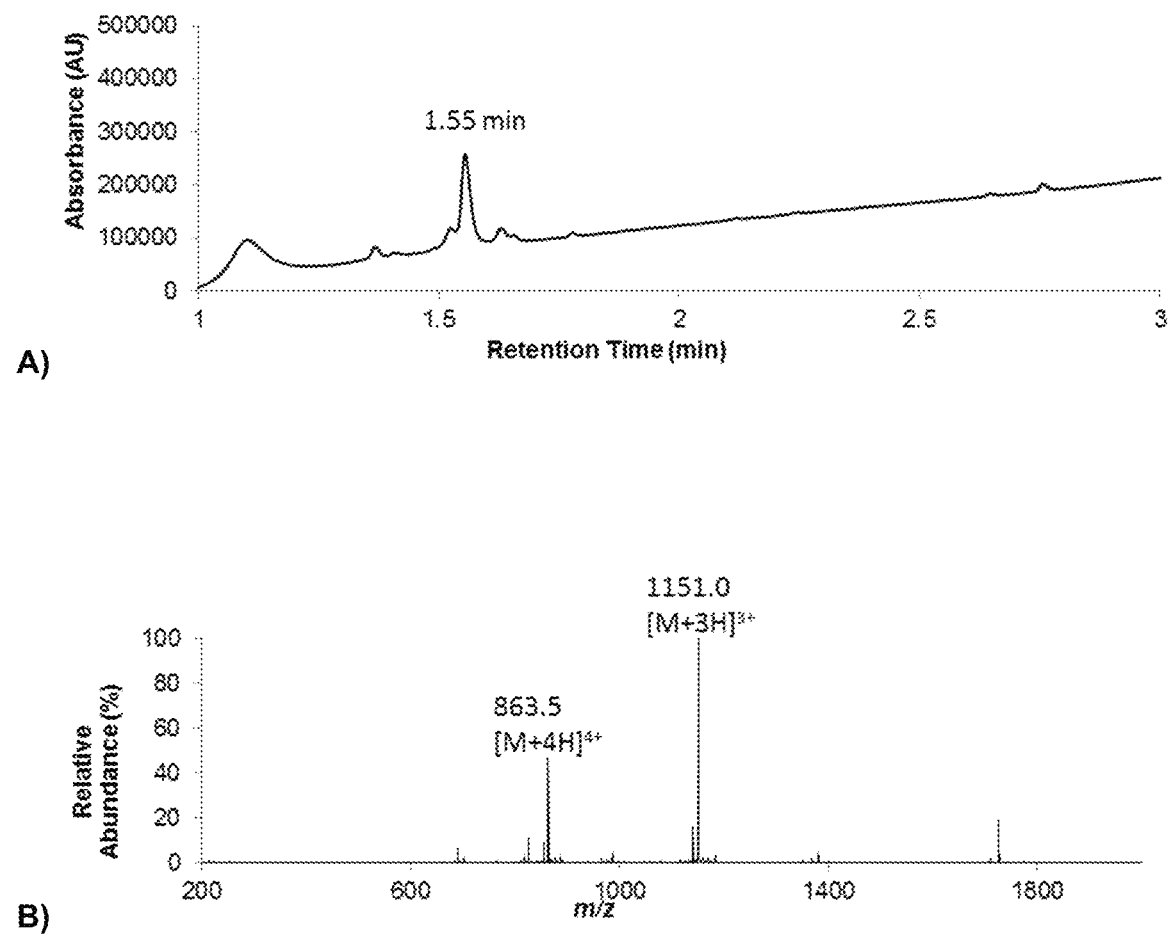
FIG. 4 A) Analytical UPLC of $A^{4a}$ (1-30) fragment 87: $R_t$ 1.55 min (0 to 60% B over 3 min, Eluent B, $\lambda$=230 nm); B) Mass spectrum (ESI+) of 87: Calculated mass for (neutral) $C_{142}H_{210}N_{33}O_{61}S$ [M]: 3386.4, $[M+3H]^{3+}$: 1150.8 (100%), $[M+4H]^{4+}$: 863.6 (100.0%); Mass Found (ESI+) $[M+3H]^{3+}$: 1151.0, $[M+4H]^{4+}$: 863.5.

Fmoc-Thr(OtBu)-OH (100 mg, 250 μmop was loaded onto CTC resin using standard loading procedure. Iterative Fmoc-SPPS was then carried out as outlined above to give the fully assembled resin bound $A^{Aa}$ (1-30). The peptide on resin was split and 25 μmol peptide was used in the following treatment. The protected peptide was liberated from resin using HFIP/CH$_2$Cl$_2$ (4 mL, 7:3 v/v). The resulting product was subsequently treated with PyBOP (65 mg, 0.13 mmol, 5.0 eq.), iPr$_2$NEt (22 μL, 16 mg, 0.13 mmol, 5.0 eq.), and ethyl 3-mercaptopropionate (160 μL, 170 mg, 1.3 mmol, 50 eq.) in DMF (2 mL) at −40° C. overnight. At this point the reaction mixture was concentrated in vacuo. The peptide was then deprotected with TFA/iPr$_3$SiH/H$_2$O (4 mL, 90:5:5 v/v/v) and the reaction mixture was agitated for 2 h. The resulting crude product was precipitated from ice-cold Et$_2$O (20 mL) and purified by preparative HPLC (20 to 80% B over 60 min, Eluent A) to afford peptide thioester 87 as a TFA salt (11 mg, 12%) after lyophilisation. See FIGS. 4A & B.

General Procedure for One-Pot Synthesis of Disulfated $A^{Aa}$

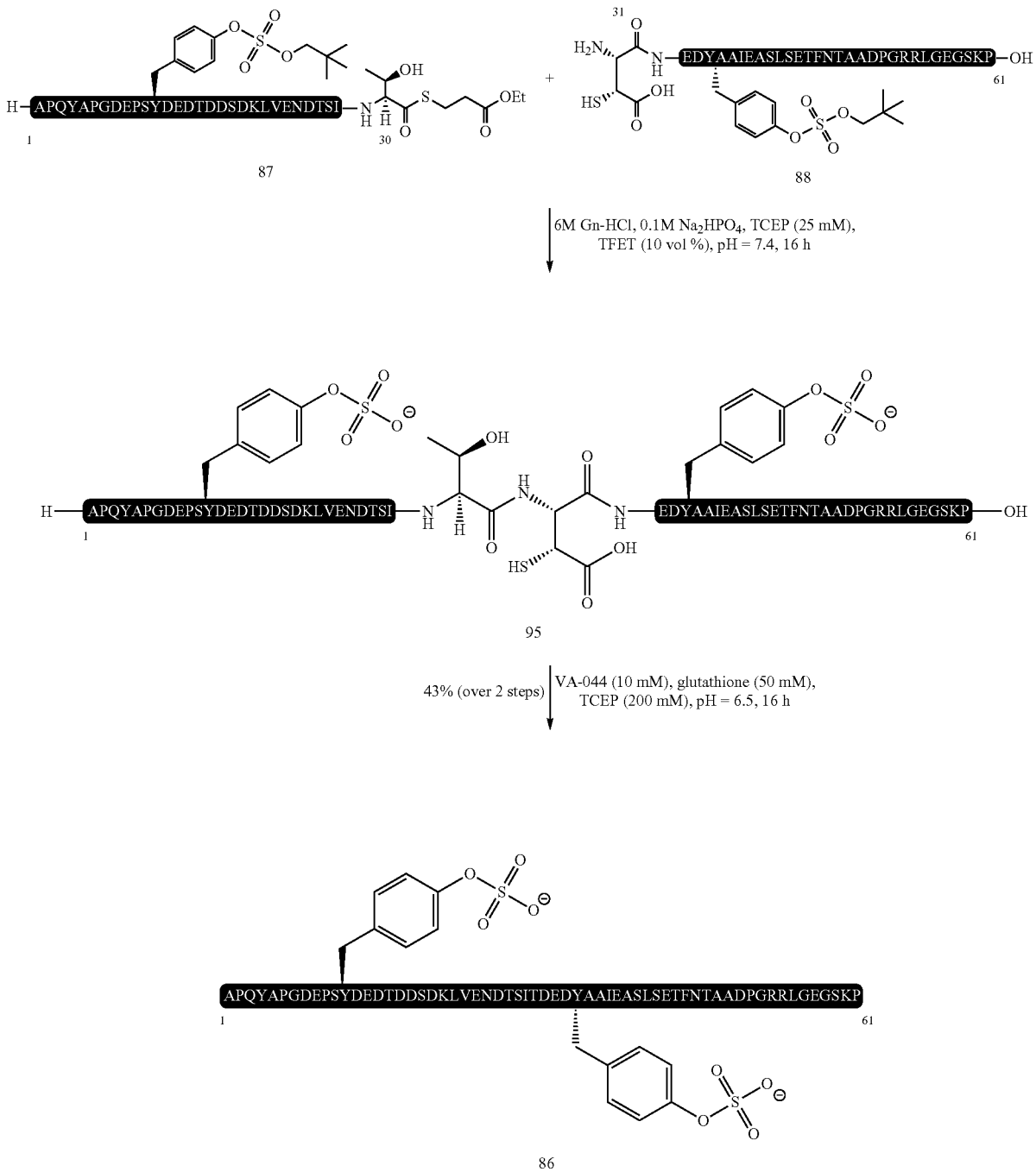

Scheme 3 One-Pot Synthesis of Doubly Sulfated $A^{Aa}$ (86)

Figures 5A, 5B:
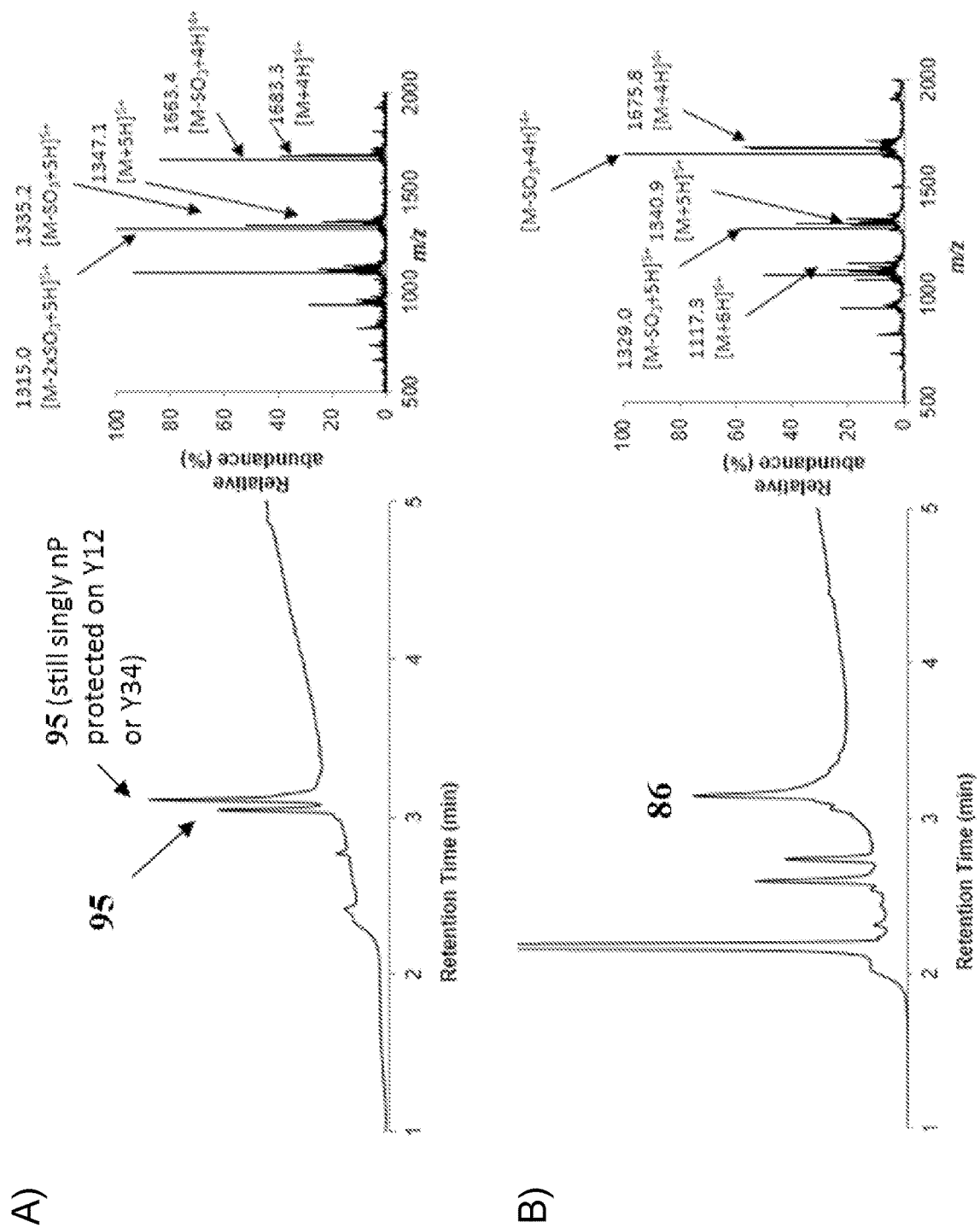
FIG. 5. A) Crude UPLC-MS analysis of ligation reaction between the C-terminal $A^{4a}$ (31-61) fragment 87 and $A^{4a}$ (1-30) peptide thioester 86 to give the corresponding ligation product 95 ($\lambda$=230 nm). Mass calculated for 95 (100% relative abundance) $[M+4H]^{4+}$: 1683.2, $[M+5H]^{5+}$: 1346.7, Mass found (ESI+) m/z: $[M+4H]^{4+}$: 1683.3, $[M+5H]^{5+}$: 1347.1. B) Crude UPLC-MS analysis of the in situ desulfurization reaction of ligation product 95 after 16 h to give the corresponding disulfated $A^{4a}$ (86). Mass calculated for 86 (100% relative abundance) $[M+4H]^{4+}$: 1675.2, $[M+5H]^{5+}$: 1340.4, $[M+6H]^{6+}$: 1117.1, Mass found (ESI+) m/z: $[M+4H]^{4+}$: 1675.8, $[M+5H]^{5+}$: 1340.9, $[M+6H]^{6+}$: 1117.3.
Figures 6A, 6B:
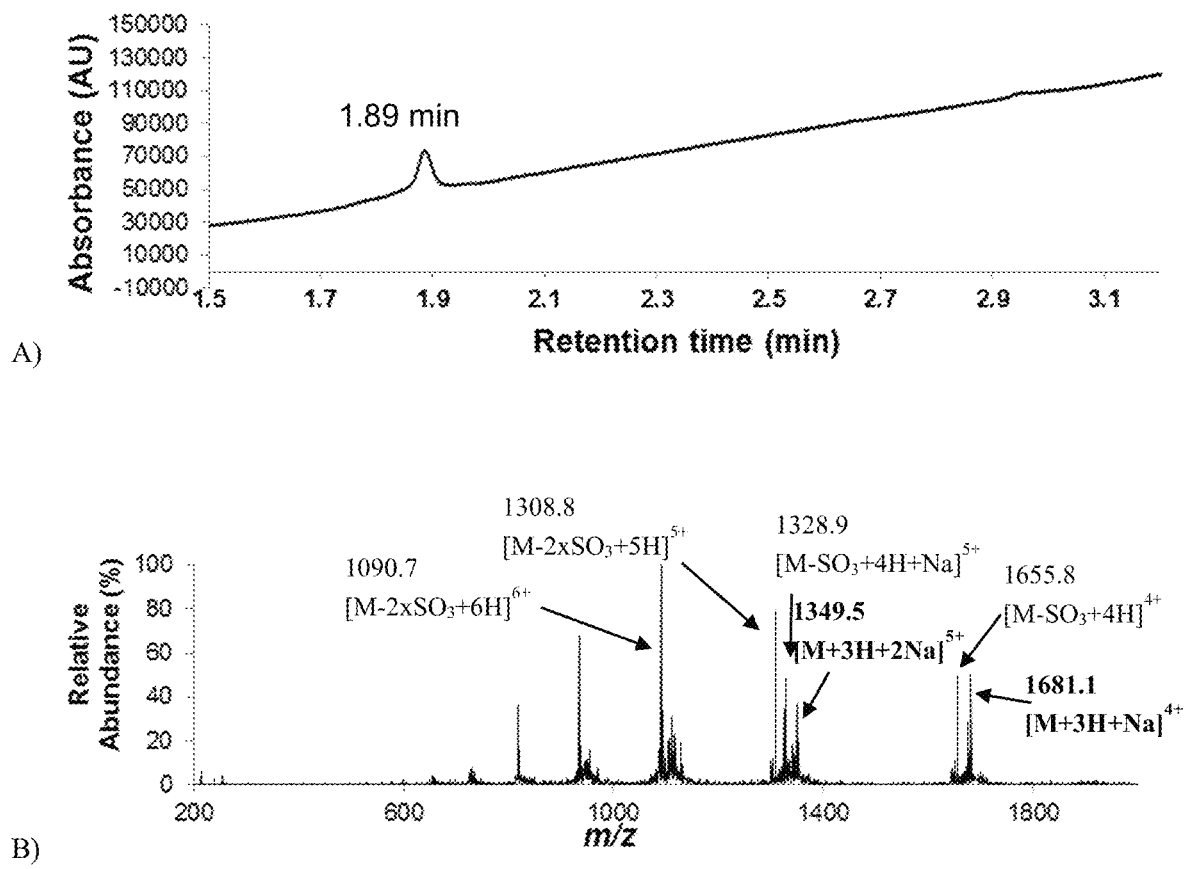
FIG. 6 A) Analytical UPLC of doubly sulfated $A^{4a}$ (86): $R_t$ 1.89 min (0 to 60% B over 3 min, Eluent B, $\lambda$=214 nm); B) Mass spectrum (ESI+) of 86: Calculated mass for protonated (neutral) $C_{275}H_{416}N_{72}O_{119}S_2$ [M]: 6696.8, $[M+3H+Na]^{4+}$: 1680.7 (100%), $[M+3H+2Na]^{5+}$: 1349.2 (100.0%); Mass Found (ESI+) $[M+3H+Na]^{4+}$: 1681.1, $[M+3H+2Na]^{5+}$: 1349.5. HRMS (MALDI) 6697.789 (avg.) calculated for $[C_{275}H_{416}N_{72}O_{119}S_2-H]^-$, found 6698.295.

A solution of peptide 88 (6.0 mg, 1.6 μmol, 1.2 eq.) in ligation buffer (6 M Gn.HCl, 100 mM Na$_2$HPO$_4$, 25 mM TCEP, pH 6.8, 320 μL) was added to peptide thioester 87 (5 mg, 1.3 μmol, 1.0 eq.) to give a final 5 mM solution of peptide thioester 87. The resulting solution was carefully readjusted to pH 7.4 with 2 M NaOH followed by addition of TFET (10 vol. %) and incubated at 30° C. for 2 h. UPLC-MS analysis indicated complete conversion to the ligated protein 95. A neutral solution of TCEP (0.5 M) and glutathione (100 mM) in buffer (6 M Gn.HCl, 100 mM Na$_2$PO$_4$, 320 μL) was then added to give a 2.5 mM final concentration of the ligation product. The resulting solution was adjusted to pH 6.5 and then degassed by sparging with Ar for 10 min which also removed the excess TFET from the reaction mixture. VA-044 (10 mM) was then added in solid form and the reaction mixture was gently agitated and incubated at 37° C. for 16 h. After this time, UPLC-MS analysis showed a complete conversion to the doubly sulfated $A^{Aa}$ 86. The crude reaction mixture was subjected to preparative HPLC purification (0 to 60% B over 60 min, 0.1 M NH$_4$OAc) to afford disulfated $A^{Aa}$ 86 as an ammonium acetate salt (3.9 mg, 43%) after lyophilisation. See FIG. 5.

REFERENCES

World Health Organization (2014), Fact Sheet No. 310, The top 10 causes of death (updated May 2014).

Wardlaw J M, et al. (2012). Recombinant tissue plasminogen activator for acute ischaemic stroke: an updated systematic review and meta-analysis. Lancet. 379(9834): 2364-72.

Molina C A, Saver J L. (2005). Extending reperfusion therapy for acute ischemic stroke emerging pharmacological, mechanical, and imaging strategies. Stroke. 36(10):2311-20.

Alexandrov A V, Grotta J C. (2002). Arterial reocclusion in stroke patients treated with intravenous tissue plasminogen activator. Neurology. 59(6):862-7.

Rubiera M, et al. (2005). Predictors of early arterial reocclusion after tissue plasminogen activator-induced recanalization in acute ischemic stroke. Stroke. 36(7):1452-6.

Barreto A D, et al. (2012). The argatroban and tissue-type plasminogen activator stroke study final results of a pilot safety study. Stroke. 43(3):770-5.

von Kummer R, Hacke W. (1992) Safety and efficacy of intravenous tissue plasminogen activator and heparin in acute middle cerebral artery stroke. Stroke. 23(5):646-52.

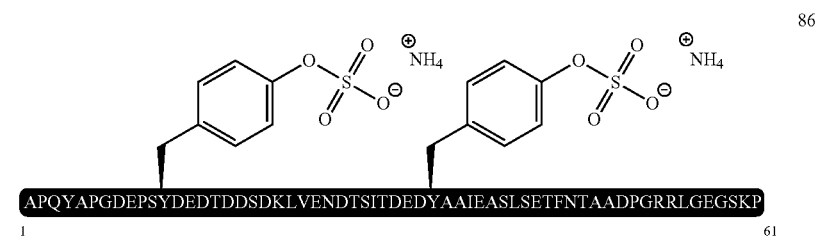

Example 3—Clotting and Bleeding Time of $A^{Aa}$ Compared with Hirudin

We investigated the ability of the inhibitor of Example 2 ($A^{Aa}$) to prolong clotting time in an in vitro activated partial thromboplastin time (APTT) assay (FIG. 1A). These studies have demonstrated that while hirudin exhibited an 8-fold increase in clotting time at concentrations above 2 μg/mL, $A^{Aa}$ (5.7-fold) remained within a safer clotting time range.

Figures 1C, 1D:
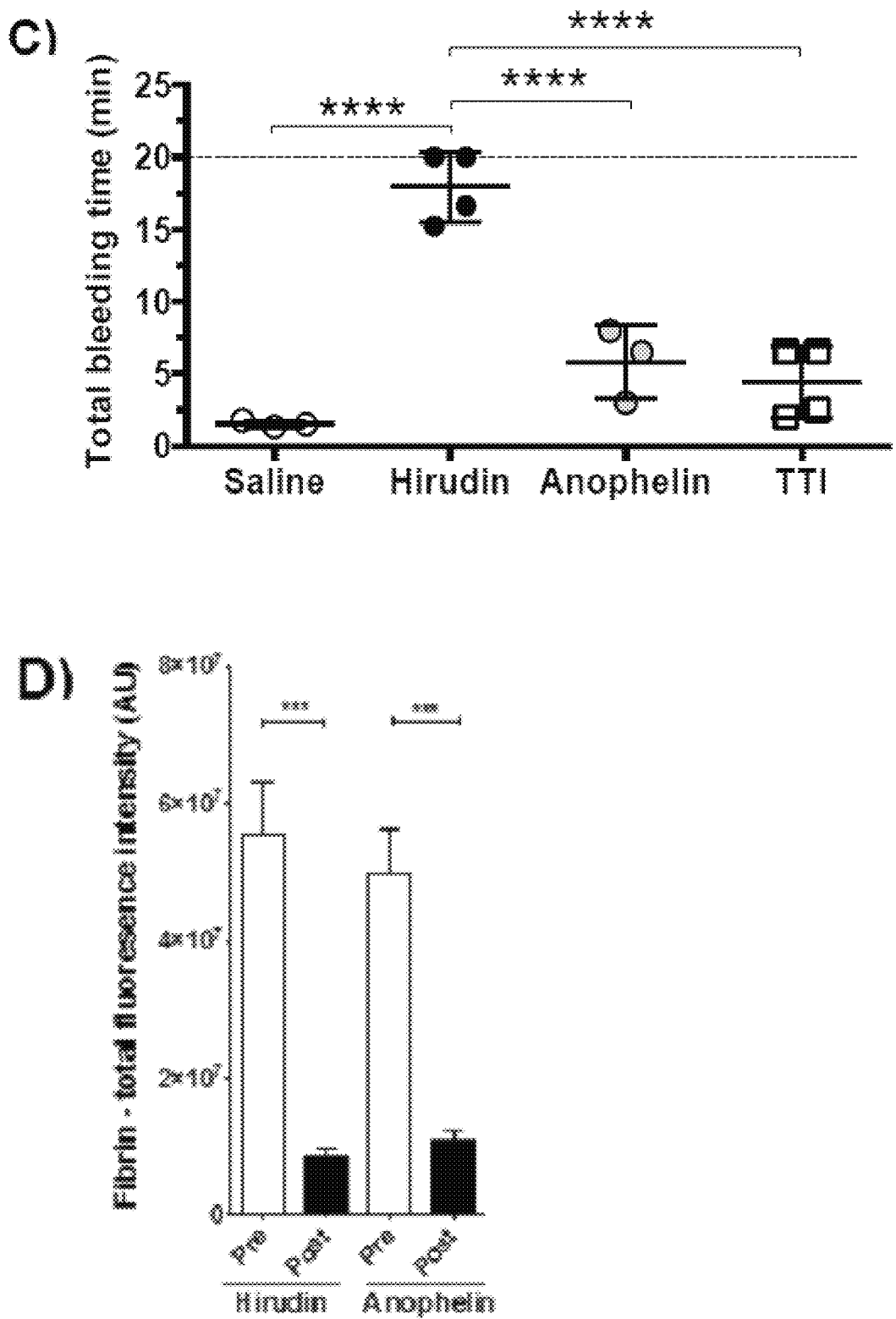
Figure 1E:
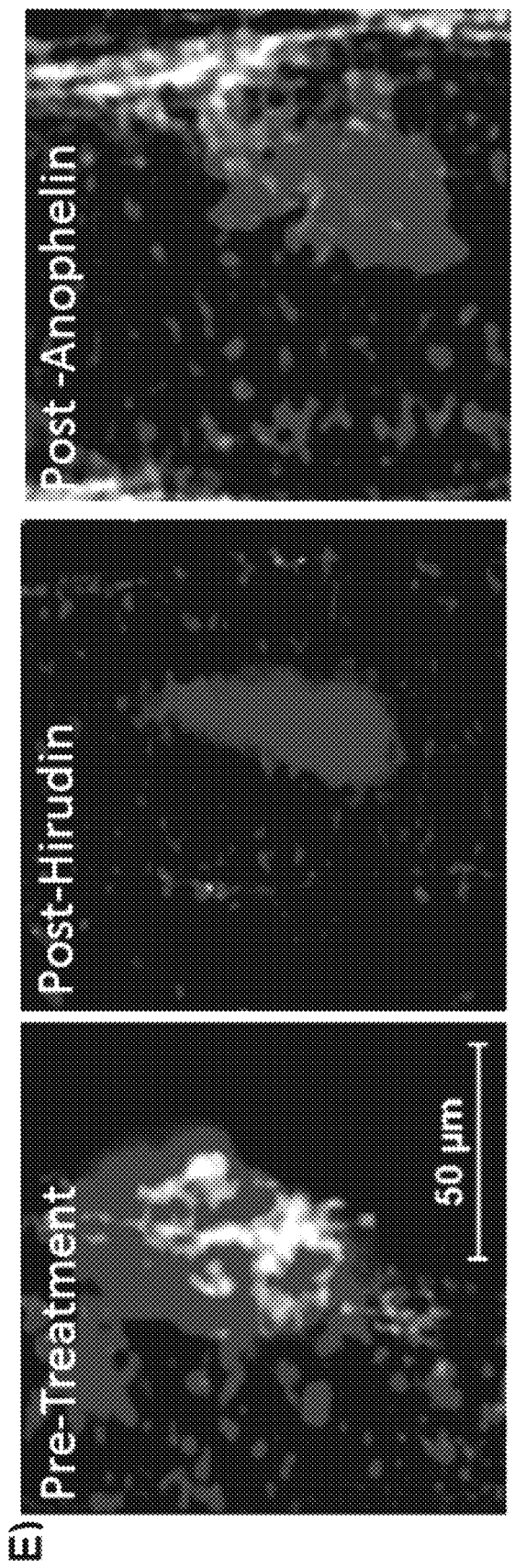

We have additionally shown that whilst $A^{Aa}$ possesses very similar antithrombotic activity to hirudin in an in vivo needle injury model (FIG. 1B), it exhibits over 3-fold less bleeding in a tail bleed in vivo model (FIG. 10). Whilst $A^{Aa}$ is similarly effective to hirudin at removing fibrin from the thrombus (FIG. 1D), it appears to be less effective at removing platelets (see FIG. 1E for confocal images of hirudin and $A^{Aa}$). This differential effect on fibrin and platelets was unexpected and may partially explain the significant decrease in bleeding observed with $A^{Aa}$.

Example 4—Inhibition of Thrombin by Sulphated Forms of $A^{Aa}$

Figure 2:
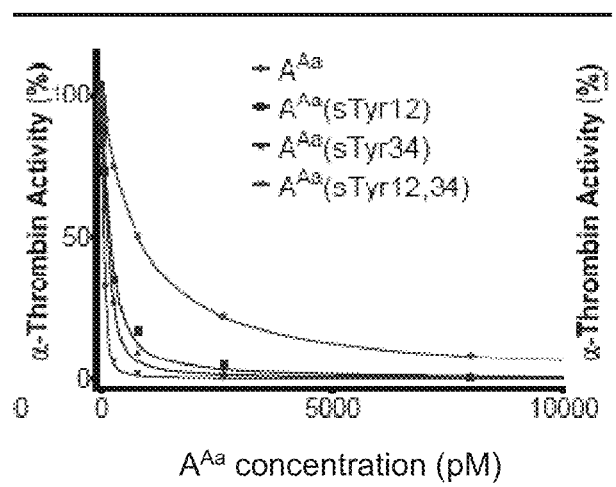
FIG. 2. Table of inhibition constants (Ki) of the sulfated thrombin inhibitors accompanied by raw inhibition data.

The inventors demonstrate, as shown in FIG. 2a, that sulfated peptides inhibit thrombin with a K of less than about 6 pM, for example less than 3.0 pM. Further, doubly sulfated variants of these peptides and proteins are over two orders of magnitude more potent as inhibitors of human thrombin in vitro than the unsulfated counterparts.

Jang I-K, et al. (1999). A multicenter, randomized study of argatroban versus heparin as adjunct to tissue plasminogen activator (tPA) in acute myocardial infarction: myocardial infarction with novastan and tPA (MINT) study. J. Am. Coll. Cardiol. 33(7):1879-85.

Karabiyikoglu M, Hua Y, Keep R F, Ennis S R, Xi G. (2004). Intracerebral hirudin injection attenuates ischemic damage and neurologic deficits without altering local cerebral blood flow. J. Cereb. Blood Flow Metab. 24(2):159-66.

Lovely R S, et al 2002 J. Thrombosis and Haemostasis 1: 124-131.

Ziarek, J. J.; Getschman, A. E.; Butler, S. J.; Taleski, D.; Stephens, B.; Kufareva, I.; Handel T. M.; Payne, R. J.; Volkman, B. F. Sulfopeptide Probes of the CXCR4/CXCL12 Interface Reveal Oligomer-Specific Contacts and Chemokine Allostery, ACS Chem. Biol. 2013, 8(9), 1955-1963.

Taleski, D.; Butler, S. J.; Stone, M. J.; Payne, R. J. Divergent and Site-Selective Solid-Phase Synthesis of Sulfopeptides. Chem. Asian J. 2011, 6(6), 1316-1320.

Hsieh, Y. S.; Wilkinson, B. L.; Wijeyewickrema, L. C.; Pike, R. N.; Payne, R. J. Total Synthesis of Homogeneous Variants of Hirudin P6: A Post-Translationally Modified Anti-Thrombotic Leech-Derived Protein. Angew. Chem. Int. Ed. 2014, 53, 3947-3951

The claims defining the invention are as follows:

1. A peptide comprising the amino acid sequence ZXZYZXYZXXX (SEQ ID NO: 2), wherein Z is any amino acid selected from D, E, Q, S or P and X is any amino acid, wherein at least one residue of SEQ ID NO: 2 is a sulphated tyrosine wherein the peptide comprises the amino acid sequence as set forth in any one of SEQ ID NOs: 28-38 or SEQ ID NOs: 40-44.

2. The peptide of claim 1, wherein the peptide binds to exosite II of thrombin.

3. The peptide of claim 1, wherein the peptide competitively inhibits the binding of clot-associated fibrin.

4. The peptide of claim 1, wherein the tyrosine at position 4 in SEQ ID NO: 2 is sulphated.

5. The peptide of claim 1, wherein the tyrosine at position 7 in SEQ ID NO: 2 is sulphated.

6. The peptide of claim 1, wherein the peptide consists of the amino acid sequence of as set forth in any one of SEQ ID Nos: 28-38 or SEQ ID Nos: 40-44.

7. The peptide of claim 1, wherein the peptide is no more than 35 amino acids in length.

8. The peptide of claim 3, wherein the peptide competitively inhibits the binding of fibrinogen γ' to exosite II of thrombin.

9. The peptide of claim 1, wherein the tyrosine residues at positions 4 and 7 of SEQ ID NO: 2 are sulphated.

10. The peptide of claim 1, wherein the peptide comprises the amino acid sequence DADYDDYDEEG (SEQ ID NO: 31).

11. The peptide claim 1, wherein the peptide comprises the amino acid sequence DGDYDEYDNDE (SEQ ID NO: 29).

12. The peptide claim 1, wherein the peptide comprises 49-F the amino acid sequence DADYDEYEEDG (SEQ ID NO: 28).

13. The peptide of claim 1, wherein the peptide the amino acid sequence DADYDDYDEEG (SEQ ID NO: 31).

14. The peptide of claim 1, wherein the peptide the amino acid sequence DGDYDEYDNDE (SEQ ID NO: 29).

15. The peptide claim 1, wherein the peptide the amino acid sequence DADYDEYEEDG (SEQ ID NO: 28).

16. A thrombin inhibitor of Formula 1:
wherein:
A is the peptide of claim 1;
B is a peptide having a sequence shown in any one of SEQ ID NOS: 15 to 24 for binding to the thrombin active site to prevent the thrombin active site from cleaving fibrinogen to form fibrin; and
wherein A and B are linked so as to enable A to bind to exosite II of thrombin when B is bound to the thrombin active site.

17. The thrombin inhibitor of claim 16, wherein the thrombin inhibitor provides for a bleeding time or a clotting time that is at least 20% shorter than hirudin on a molar equivalent basis of the peptide and hirudin.

18. The peptide of claim 16, wherein the peptide comprises the amino acid sequence of DGDYDEYDNDE (SEQ ID NO: 29).

19. The peptide of claim 16, wherein the tyrosine residues at positions 4 and 7 of SEQ ID NO: 2 are sulphated.

20. A pharmaceutical composition including a peptide of claim 1, together with a pharmaceutically effective carrier, diluent or excipient.

21. A method of thrombolytic therapy comprising administering a therapeutically effective amount of a peptide of claim 1 to a subject in need thereof.

22. The method of claim 21, wherein the thrombolytic therapy includes tPA therapy.

* * * * *

UNITED STATES PATENT AND TRADEMARK OFFICE
CERTIFICATE OF CORRECTION

PATENT NO. : 11,091,535 B2
APPLICATION NO. : 16/469804
DATED : August 17, 2021
INVENTOR(S) : Richard J. Payne et al.

It is certified that error appears in the above-identified patent and that said Letters Patent is hereby corrected as shown below:

In the Claims

In Claim 12, Column 53, Line 44, delete "49-F".

In Claim 13, Column 54, Line 12, delete "the peptide the amino" and insert --the peptide consists of the amino-- therefor.

In Claim 14, Column 54, Line 14, delete "the peptide the amino" and insert --the peptide consists of the amino-- therefor.

In Claim 15, Column 54, Line 16, delete "the peptide the amino" and insert --the peptide consists of the amino-- therefor.

In Claim 16, Column 54, Line 19, delete "wherein:" and insert
--A - B
wherein:-- therefor.

Signed and Sealed this
Ninth Day of November, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 44

<210> SEQ ID NO 1
<211> LENGTH: 14
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (2)..(2)
<223> OTHER INFORMATION: is any amino acid
<220> FEATURE:
<221> NAME/KEY: MISC_FEATURE
<222> LOCATION: (4)..(6)
<223> OTHER INFORMATION: is any amino acid
<220> FEATURE:
<221> NAME/KEY: MISC_FEATURE
<222> LOCATION: (7)..(8)
<223> OTHER INFORMATION: is D, E, Q, S or P
<220> FEATURE:
<221> NAME/KEY: MISC_FEATURE
<222> LOCATION: (10)..(10)
<223> OTHER INFORMATION: is any amino acid
<220> FEATURE:
<221> NAME/KEY: MISC_FEATURE
<222> LOCATION: (12)..(14)
<223> OTHER INFORMATION: is D, E, Q, S or P

<400> SEQUENCE: 1

Pro Xaa Tyr Xaa Xaa Xaa Xaa Xaa Pro Xaa Tyr Xaa Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D, E, Q, S or P
<220> FEATURE:
<221> NAME/KEY: MISC_FEATURE
<222> LOCATION: (2)..(2)
<223> OTHER INFORMATION: is any amino acid
<220> FEATURE:
<221> NAME/KEY: MISC_FEATURE
<222> LOCATION: (3)..(3)
<223> OTHER INFORMATION: is D, E, Q, S or P
<220> FEATURE:
<221> NAME/KEY: MISC_FEATURE
<222> LOCATION: (5)..(5)
<223> OTHER INFORMATION: is D, E, Q, S or P
<220> FEATURE:
<221> NAME/KEY: MISC_FEATURE
<222> LOCATION: (6)..(6)
<223> OTHER INFORMATION: is any amino acid
<220> FEATURE:
<221> NAME/KEY: MISC_FEATURE
<222> LOCATION: (8)..(8)
<223> OTHER INFORMATION: is D, E, Q, S or P
<220> FEATURE:
<221> NAME/KEY: MISC_FEATURE
<222> LOCATION: (9)..(11)
<223> OTHER INFORMATION: is any amino acid

<400> SEQUENCE: 2

Xaa Xaa Xaa Tyr Xaa Xaa Tyr Xaa Xaa Xaa Xaa
1               5                   10

<210> SEQ ID NO 3
<211> LENGTH: 14

```
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (2)..(2)
<223> OTHER INFORMATION: is K/ R/ H
<220> FEATURE:
<221> NAME/KEY: MISC_FEATURE
<222> LOCATION: (4)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/ E
<220> FEATURE:
<221> NAME/KEY: MISC_FEATURE
<222> LOCATION: (10)..(10)
<223> OTHER INFORMATION: is any amino acid
<220> FEATURE:
<221> NAME/KEY: MISC_FEATURE
<222> LOCATION: (12)..(14)
<223> OTHER INFORMATION: is D/ E

<400> SEQUENCE: 3

Pro Xaa Tyr Xaa Xaa Gly Xaa Xaa Pro Xaa Tyr Xaa Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (4)..(4)
<223> OTHER INFORMATION: is A/T/S or G
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
<221> NAME/KEY: MISC_FEATURE
<222> LOCATION: (10)..(10)
<223> OTHER INFORMATION: is S or T
<220> FEATURE:
<221> NAME/KEY: MISC_FEATURE
<222> LOCATION: (12)..(14)
<223> OTHER INFORMATION: is D/E

<400> SEQUENCE: 4

Pro Gln Tyr Xaa Xaa Gly Xaa Xaa Pro Xaa Tyr Xaa Xaa Xaa
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
```

```
<221> NAME/KEY: MISC_FEATURE
<222> LOCATION: (10)..(10)
<223> OTHER INFORMATION: is S/T
<220> FEATURE:
<221> NAME/KEY: MISC_FEATURE
<222> LOCATION: (12)..(14)
<223> OTHER INFORMATION: is D/E

<400> SEQUENCE: 5

Pro Gln Tyr Ala Xaa Gly Xaa Xaa Pro Xaa Tyr Xaa Xaa Xaa
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
<221> NAME/KEY: MISC_FEATURE
<222> LOCATION: (10)..(10)
<223> OTHER INFORMATION: is S/T
<220> FEATURE:
<221> NAME/KEY: MISC_FEATURE
<222> LOCATION: (12)..(14)
<223> OTHER INFORMATION: is D/E
<220> FEATURE:
<221> NAME/KEY: MISC_FEATURE
<222> LOCATION: (15)..(18)
<223> OTHER INFORMATION: is any amino acid
<220> FEATURE:
<221> NAME/KEY: MISC_FEATURE
<222> LOCATION: (19)..(19)
<223> OTHER INFORMATION: is D/E
<220> FEATURE:
<221> NAME/KEY: MISC_FEATURE
<222> LOCATION: (20)..(21)
<223> OTHER INFORMATION: is any amino acid

<400> SEQUENCE: 6

Pro Gln Tyr Ala Xaa Gly Xaa Xaa Pro Xaa Tyr Xaa Xaa Xaa Xaa
1               5                   10                  15

Xaa Xaa Xaa Xaa Xaa
            20

<210> SEQ ID NO 7
<211> LENGTH: 21
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
<221> NAME/KEY: MISC_FEATURE
<222> LOCATION: (10)..(10)
<223> OTHER INFORMATION: is S/T
<220> FEATURE:
<221> NAME/KEY: MISC_FEATURE
<222> LOCATION: (12)..(14)
```

```
<223> OTHER INFORMATION: is D or E
<220> FEATURE:
<221> NAME/KEY: MISC_FEATURE
<222> LOCATION: (15)..(15)
<223> OTHER INFORMATION: is D/T
<220> FEATURE:
<221> NAME/KEY: MISC_FEATURE
<222> LOCATION: (16)..(16)
<223> OTHER INFORMATION: is D/G/F
<220> FEATURE:
<221> NAME/KEY: MISC_FEATURE
<222> LOCATION: (17)..(17)
<223> OTHER INFORMATION: is D/A
<220> FEATURE:
<221> NAME/KEY: MISC_FEATURE
<222> LOCATION: (18)..(18)
<223> OTHER INFORMATION: is S/D/E
<220> FEATURE:
<221> NAME/KEY: MISC_FEATURE
<222> LOCATION: (19)..(19)
<223> OTHER INFORMATION: is D/E
<220> FEATURE:
<221> NAME/KEY: MISC_FEATURE
<222> LOCATION: (20)..(20)
<223> OTHER INFORMATION: is K/P/S
<220> FEATURE:
<221> NAME/KEY: MISC_FEATURE
<222> LOCATION: (21)..(21)
<223> OTHER INFORMATION: is L/V

<400> SEQUENCE: 7

Pro Gln Tyr Ala Xaa Gly Xaa Xaa Pro Xaa Tyr Xaa Xaa Xaa Xaa Xaa
1               5                   10                  15

Xaa Xaa Xaa Xaa Xaa
            20

<210> SEQ ID NO 8
<211> LENGTH: 21
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
<221> NAME/KEY: MISC_FEATURE
<222> LOCATION: (10)..(10)
<223> OTHER INFORMATION: is S/T
<220> FEATURE:
<221> NAME/KEY: MISC_FEATURE
<222> LOCATION: (12)..(14)
<223> OTHER INFORMATION: is D/E
<220> FEATURE:
<221> NAME/KEY: MISC_FEATURE
<222> LOCATION: (20)..(20)
<223> OTHER INFORMATION: is K/P/S
<220> FEATURE:
<221> NAME/KEY: MISC_FEATURE
<222> LOCATION: (21)..(21)
<223> OTHER INFORMATION: is L/V

<400> SEQUENCE: 8

Pro Gln Tyr Ala Xaa Gly Xaa Xaa Pro Xaa Tyr Xaa Xaa Xaa Asp Asp
1               5                   10                  15

Asp Asp Asp Xaa Xaa
            20
```

```
<210> SEQ ID NO 9
<211> LENGTH: 21
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (5)..(5)
<223> OTHER INFORMATION: is any amino acid
<220> FEATURE:
<221> NAME/KEY: MISC_FEATURE
<222> LOCATION: (7)..(8)
<223> OTHER INFORMATION: is D/E
<220> FEATURE:
<221> NAME/KEY: MISC_FEATURE
<222> LOCATION: (10)..(10)
<223> OTHER INFORMATION: is S/T
<220> FEATURE:
<221> NAME/KEY: MISC_FEATURE
<222> LOCATION: (12)..(14)
<223> OTHER INFORMATION: is D/E
<220> FEATURE:
<221> NAME/KEY: MISC_FEATURE
<222> LOCATION: (20)..(20)
<223> OTHER INFORMATION: is K/P/S
<220> FEATURE:
<221> NAME/KEY: MISC_FEATURE
<222> LOCATION: (21)..(21)
<223> OTHER INFORMATION: is L/V

<400> SEQUENCE: 9

Pro Gln Tyr Ala Xaa Gly Xaa Xaa Pro Xaa Tyr Xaa Xaa Xaa Asp Asp
1               5                   10                  15

Asp Glu Glu Xaa Xaa
            20

<210> SEQ ID NO 10
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 10

Pro Gln Tyr Ala Pro Gly Asp Glu Pro Ser Tyr Asp Glu Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 11

Pro Gln Tyr Ala Pro Gly Glu Glu Pro Ser Tyr Asp Glu Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 12

Pro Gln Tyr Thr His Gly Glu Glu Pro Glu Tyr Asp Glu Asp
1               5                   10
```

```
<210> SEQ ID NO 13
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 13

Pro Gln Tyr Ala Gln Gly Glu Glu Pro Thr Tyr Asp Glu Asp
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 14

Pro Gln Tyr Ala Arg Gly Asp Val Pro Thr Tyr Asp Glu Glu
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Thrombin inhibitor

<400> SEQUENCE: 15

Leu Thr Tyr Thr Asp
1               5

<210> SEQ ID NO 16
<211> LENGTH: 5
<212> TYPE: PRT
<213> ORGANISM: Artificial Sequence
<220> FEATURE:
<223> OTHER INFORMATION: Thrombin inhibitor

<400> SEQUENCE: 16

Val Val Tyr Thr Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Thrombin inhibitor

<400> SEQUENCE: 17

Asp Pro Gly Arg Arg Leu Gly Glu
1               5

<210> SEQ ID NO 18
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 18

Val Ala Glu Pro Lys Met
1               5

<210> SEQ ID NO 19
```

```
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 19

Glu Ile Pro Gly Ile Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 20

Pro Thr Ala Lys Pro Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 21

Arg Ala Leu His Val Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 22

Glu Pro Ala Lys Pro Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 23

Pro Arg Gly Gly Pro Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 24

Thr Leu Ile Ser Ala Arg
1               5

<210> SEQ ID NO 25
<211> LENGTH: 11
```

```
<212> TYPE: PRT
<213> ORGANISM: Artificial Sequence
<220> FEATURE:
<223> OTHER INFORMATION: Thrombin inhibitor

<400> SEQUENCE: 25

Asp Phe Glu Glu Ile Pro Glu Glu Tyr Leu Gln
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Thrombin inhibitor

<400> SEQUENCE: 26

Glu Asp Tyr Ala Ala Ile Glu Ala Ser Leu Ser Glu Thr Phe
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Thrombin inhibitor

<400> SEQUENCE: 27

Pro Phe Asp Phe Glu Ala Ile Pro Glu Glu Tyr Leu Asp Asp Glu Ser
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 28

Asp Ala Asp Tyr Asp Glu Tyr Glu Glu Asp Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 29

Asp Gly Asp Tyr Asp Glu Tyr Asp Asn Asp Glu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 30

Gln Gly Asp Tyr Asp Glu Tyr Asp Gln Asp Glu
1               5                   10

<210> SEQ ID NO 31
<211> LENGTH: 11
<212> TYPE: PRT
```

```
<213> ORGANISM: Artificial Sequence
<220> FEATURE:
<223> OTHER INFORMATION: Thrombin inhibitor

<400> SEQUENCE: 31

Asp Ala Asp Tyr Asp Asp Tyr Asp Glu Glu Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 32

Asp Val Ser Tyr Asp Glu Tyr Glu Asp Asn Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 33

Gln Asp Asp Tyr Asp Glu Tyr Asp Ala Asp Glu
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 34

Glu Thr Asp Tyr Asp Glu Tyr Glu Glu Asn Glu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 35

Glu Ser Asp Tyr Asp Thr Tyr Pro Asp Asp Asn
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 36

Asp Asp Glu Tyr Asp Met Tyr Glu Ser Asp Gly
1               5                   10

<210> SEQ ID NO 37
<211> LENGTH: 11
<212> TYPE: PRT
<213> ORGANISM: Artificial Sequence
```

```
<220> FEATURE:
<223> OTHER INFORMATION: Thrombin inhibitor

<400> SEQUENCE: 37

Glu Thr Ser Tyr Glu Glu Tyr Pro Asp Asp Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 38

Glu Ser Asp Tyr Asp Thr Tyr Pro Asp Asp Asn
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Thrombin inhibitor

<400> SEQUENCE: 39

Glu Arg Asp Asp Glu Asp Tyr Asp Asn Ser Asn
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D/E
<220> FEATURE:
<221> NAME/KEY: MISC_FEATURE
<222> LOCATION: (2)..(2)
<223> OTHER INFORMATION: is T/M/E/S/D/G/N/P
<220> FEATURE:
<221> NAME/KEY: MISC_FEATURE
<222> LOCATION: (3)..(3)
<223> OTHER INFORMATION: is D/E
<220> FEATURE:
<221> NAME/KEY: MISC_FEATURE
<222> LOCATION: (5)..(6)
<223> OTHER INFORMATION: is D/E
<220> FEATURE:
<221> NAME/KEY: MISC_FEATURE
<222> LOCATION: (8)..(11)
<223> OTHER INFORMATION: is D/E

<400> SEQUENCE: 40

Xaa Xaa Xaa Tyr Xaa Xaa Tyr Xaa Xaa Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D/E
<220> FEATURE:
```

```
<221> NAME/KEY: MISC_FEATURE
<222> LOCATION: (3)..(3)
<223> OTHER INFORMATION: is D/E
<220> FEATURE:
<221> NAME/KEY: MISC_FEATURE
<222> LOCATION: (5)..(5)
<223> OTHER INFORMATION: is D/E

<400> SEQUENCE: 41

Xaa Ser Xaa Tyr Xaa Thr Tyr Pro Asp Asp Asn
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D/E
<220> FEATURE:
<221> NAME/KEY: MISC_FEATURE
<222> LOCATION: (3)..(3)
<223> OTHER INFORMATION: is D/E
<220> FEATURE:
<221> NAME/KEY: MISC_FEATURE
<222> LOCATION: (5)..(5)
<223> OTHER INFORMATION: is D/E

<400> SEQUENCE: 42

Xaa Asp Xaa Tyr Xaa Met Tyr Glu Ser Asp Gly
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D/E
<220> FEATURE:
<221> NAME/KEY: MISC_FEATURE
<222> LOCATION: (5)..(5)
<223> OTHER INFORMATION: is D/E

<400> SEQUENCE: 43

Xaa Thr Ser Tyr Xaa Glu Tyr Pro Asp Asp Ser
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Thrombin inhibitor
<220> FEATURE:
<221> NAME/KEY: MISC_FEATURE
<222> LOCATION: (1)..(1)
<223> OTHER INFORMATION: is D/E
<220> FEATURE:
<221> NAME/KEY: MISC_FEATURE
<222> LOCATION: (3)..(3)
<223> OTHER INFORMATION: is D/E
<220> FEATURE:
```

```
<221> NAME/KEY: MISC_FEATURE
<222> LOCATION: (5)..(5)
<223> OTHER INFORMATION: is D/E

<400> SEQUENCE: 44

Xaa Ser Xaa Tyr Xaa Thr Tyr Pro Asp Asp Asn
1               5                   10
```